(12) United States Patent
Ferro et al.

(10) Patent No.: US 12,178,610 B2
(45) Date of Patent: Dec. 31, 2024

(54) HIP BROACH WITH EMBEDDED SENSOR AND A FEEDBACK BROACH SYSTEM

(71) Applicant: AOD Holdings, LLC, Arroyo Grande, CA (US)

(72) Inventors: Austin T. Ferro, San Luis Obispo, CA (US); Thomas D. Ferro, Arroyo Grande, CA (US); Kyle Boucher, Arroyo Grande, CA (US); Joseph R. Phillips, Paso Robles, CA (US)

(73) Assignee: AOD Holdings, LLC, Arroyo Grande, CA (US)

( * ) Notice: Subject to any disclaimer, the term of this patent is extended or adjusted under 35 U.S.C. 154(b) by 0 days.

(21) Appl. No.: 18/151,231

(22) Filed: Jan. 6, 2023

(65) Prior Publication Data

US 2023/0148967 A1    May 18, 2023

Related U.S. Application Data

(60) Continuation of application No. 16/774,791, filed on Jan. 28, 2020, now Pat. No. 11,576,615, which is a division of application No. 15/604,040, filed on May 24, 2017, now Pat. No. 10,575,781.

(60) Provisional application No. 62/340,653, filed on May 24, 2016.

(51) Int. Cl.
A61B 5/00 (2006.01)
A61B 17/16 (2006.01)
A61B 90/00 (2016.01)

(52) U.S. Cl.
CPC .......... *A61B 5/6847* (2013.01); *A61B 5/0031* (2013.01); *A61B 5/4571* (2013.01); *A61B 5/7455* (2013.01); *A61B 17/1659* (2013.01); *A61B 17/1668* (2013.01); *A61B 17/164* (2013.01); *A61B 2090/064* (2016.02); *A61B 2562/0261* (2013.01)

(58) Field of Classification Search
CPC ............ A61B 17/1659; A61B 17/1668; A61B 5/0053; A61B 5/4571; A61B 2090/064
See application file for complete search history.

(56) References Cited

U.S. PATENT DOCUMENTS

| | | |
|---|---|---|
| 4,922,898 A | 5/1990 | Dunn |
| 5,006,121 A | 4/1991 | Hafeli |
| 5,147,408 A | 9/1992 | Noble et al. |
| 6,015,408 A | 1/2000 | Pichon et al. |
| 6,074,394 A | 6/2000 | Krause |
| 6,120,508 A | 9/2000 | Grunig et al. |
| 6,503,249 B1 | 1/2003 | Krause |
| 7,001,392 B2 | 2/2006 | McGovern |

(Continued)

*Primary Examiner* — David W Bates
(74) *Attorney, Agent, or Firm* — McDonnell Boehnen Hulbert & Berghoff LLP

(57) ABSTRACT

Within examples, a surgical device with an embedded sensor system for performing hip replacements is described. This device mitigates fracturing of the mid metaphyseal/diaphyseal region of the femur, and ensures adequate press-fit of the component into the bone. The device relays information regarding forces experienced by the patient's bone to a separate data acquisition device and displays it on an interface. This information is used by the surgeon to determine the force present inside of the patient's bone during broaching, and can then be used to provide better care, and mitigate fractures due to overloading in the bone.

19 Claims, 17 Drawing Sheets

(56) References Cited

U.S. PATENT DOCUMENTS

| | | |
|---|---|---|
| 7,799,029 B2 | 9/2010 | Jones |
| 9,629,641 B2 | 4/2017 | Ferro et al. |
| 9,662,122 B2 | 5/2017 | Young |
| 10,575,781 B2 | 3/2020 | Ferro et al. |
| 11,576,615 B2 * | 2/2023 | Ferro ............... A61B 5/7455 |
| 2004/0243148 A1 | 12/2004 | Wasielewski |
| 2005/0012610 A1 | 1/2005 | Liao et al. |
| 2006/0004431 A1 | 1/2006 | Fuller et al. |
| 2006/0271112 A1 | 11/2006 | Martinson et al. |
| 2007/0179568 A1 | 8/2007 | Nycz et al. |
| 2007/0225821 A1 | 9/2007 | Reubelt et al. |
| 2010/0204802 A1 | 8/2010 | Wilson et al. |
| 2012/0216611 A1 | 8/2012 | Stein et al. |
| 2014/0081274 A1 | 3/2014 | Huff et al. |
| 2015/0142372 A1 | 5/2015 | Singh |
| 2017/0340282 A1 | 11/2017 | Ferro et al. |
| 2018/0116821 A1 * | 5/2018 | Johannaber ............ A61B 17/92 |
| 2020/0163623 A1 | 5/2020 | Ferro et al. |

\* cited by examiner

HIP BROACH WITH EMBEDDED SENSOR AND A FEEDBACK BROACH SYSTEM

CROSS REFERENCE TO RELATED APPLICATION

The present application claims priority to and is a continuation of U.S. application Ser. No. 16/774,791, filed on Jan. 28, 2020, which claims priority to and is a divisional U.S. application Ser. No. 15/604,040, filed on May 24, 2017, which claims priority to U.S. provisional application No. 62/340,653 filed on May 24, 2016, the entire disclosures of each of which are herein incorporated by reference.

FIELD

The present disclosure generally relates to a hip broach or hip rasp, and more particularly, to a hip broach that includes one or more sensors embedded within to detect a compression force as the hip broach is impacted into bone.

BACKGROUND

Hip replacement surgery is an increasingly common surgical procedure that addresses the disability that results from arthritis and other causes of pain and disability secondary to loss of function of the hip joint. Reliable and durable fixation of prosthetic hip components to the proximal (upper) femoral bone has been demonstrated utilizing porous metal surfaces press fit into the bony surfaces. This is typically performed by manually impacting a broach in the shape of the component into the proximal femoral canal. The force transferred to the bone is generally unknown and left to the discretion of the surgeon. Given the heterogeneous population undergoing hip replacement, and the wide range of bone quality and strength related to factors such as age, size, gender and the presence of osteoporosis, it would be beneficial for surgeons to know the amount of force they are applying to a femur both to prevent femoral fractures, and to ensure that adequate tight fit (or macro fixation) is achieved to ensure osseointegration (secondary micro fixation). This could potentially result in improved patient outcomes by means of preventing complications and improving surgeon precision and reproducibility in fitting femoral prostheses into bone.

SUMMARY

Within examples, the device described herein is intended for use in orthopedic hip replacement surgery. This device is a "broach" that is hammered into the patient's femur to make a pocket for a hip replacement prosthesis. This device uses sensors to indicate how much dynamic and static forces are present upon the broach as it is being hammered into the femur. The amount of force experienced by the broach is transmitted to a user interface, such as a display or computer monitor. The data can be transferred through a wired or wireless connection. This device's purpose is to mitigate fracturing of the mid metaphyseal/diaphyseal region, and to ensure adequate press-fit of the component into the bone.

In one example, a hip broach is described that includes a body having a first side, a second side, and a proximal portion, and a handle connection coupled to the proximal portion. The hip broach also includes one or more sensors positioned in the body between the first side and the second side, and the one or more sensors detect a compression of the first side toward the second side and output a signal indicative of the compression.

In another example, a system is described that includes a hip broach having one or more sensors positioned in a body of the hip broach between a first side and a second side of the body, and the one or more sensors to detect a compression of the first side toward the second side and to output a signal indicative of the compression. The system also includes one or more processors to receive the signal and to determine information indicative of a force transferred to a bone into which the hip broach is impacted based on the signal.

In another example, a method for impacting a hip broach into a femoral canal is described. The method includes detecting, by one or more sensors positioned in a body of the hip broach, a compression of a first side of the body of the hip broach toward a second side of the body of the hip broach as the hip broach is impacted into the femoral canal of a bone. The method also includes outputting a signal indicative of the compression, and determining information indicative of a force transferred to the bone based on the signal.

The features, functions, and advantages that have been discussed can be achieved independently in various examples or may be combined in yet other examples further details of which can be seen with reference to the following description and drawings.

BRIEF DESCRIPTION OF THE FIGURES

The novel features believed characteristic of the illustrative examples are set forth in the appended claims. The illustrative examples, however, as well as a preferred mode of use, further objectives and descriptions thereof, will best be understood by reference to the following detailed description of an illustrative example of the present disclosure when read in conjunction with the accompanying drawings, wherein:

DETAILED DESCRIPTION

Figure 1:
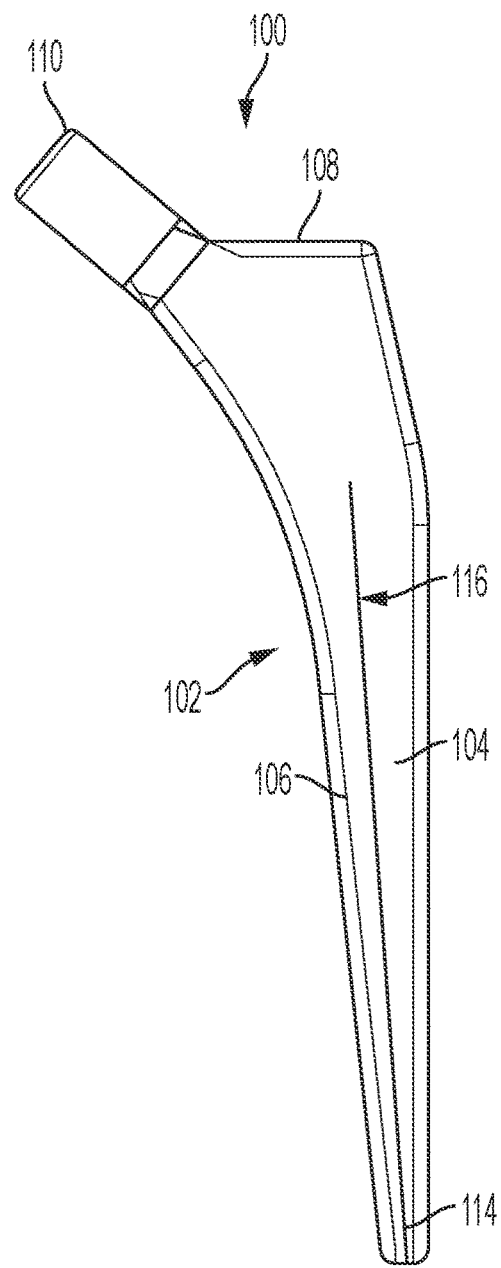
FIG. 1 illustrates a side view of an example hip broach, according to an example implementation.

Disclosed examples will now be described more fully hereinafter with reference to the accompanying drawings, in which some, but not all of the disclosed examples are shown. Indeed, several different examples may be described and should not be construed as limited to the examples set forth herein. Rather, these examples are described so that this disclosure will be thorough and complete and will fully convey the scope of the disclosure to those skilled in the art.

Within examples, a rasp or a broach for preparing a femur for a hip prosthesis implant is described that includes one or more sensors to detect a compressive load on the broach by surrounding bone as the broach is impacted into the femur. The sensor(s) can transduce, detect, or measure deflections, stresses, internal forces, strains, and other parameters resulting from the compressive load. The sensors can be used to measure both short time scale loads (e.g., such as at moment of mallet impact) and longer time scale loads (e.g., steady-state stress when the broach is lodged in the bone). The compressive load on the broach is determined, and the information is presented through a display interface audibly and/or visually to provide feedback to the surgeon during surgery. The compressive load may be related to a corresponding hoop/circumferential stress experienced by the bone and presented as feedback to the surgeon during surgery, including alerts about whether the estimated hoop stress falls in a zone of values or is above or below a threshold value.

The broach can include a gap running vertically between two parts of the broach and a sensor positioned in or near the gap such that the sensor senses a compression of the one part of the broach toward the other part directly by bridging the gap and being compressed (such as with a piezoelectric crystal transducer), detects the compression by sensing change in width of the gap due to a structure of the broach deflecting and the two parts displacing closer together (e.g. with a linear variable differential transformer (LVDT) or capacitance sensor), or detects the compression by sensing strain of a deflecting structure, or "flexure" positioned in the broach (e.g. with a load cell or strain gauge). In examples where the broach includes the flexure, the flexure comprises a portion of metal that bridges the gap at some point such that compressive load is transferred to the flexure. In other examples, the flexure could be a bending-bar or s-shaped, or a load cell, and can be machined integrally with the broach.

The broach may be driven into the bone manually with a mallet and an impactor instrument attached to the broach, or with a powered instrument. The compression sensed is along one or more axes that are substantially perpendicular to a direction of force of impaction applied to the broach.

Sensor signals are provided to a signal processing and amplification circuit, and then converted to digital data by analog-to-digital converters. The digital data is provided to a processor. The processor controls indicators for the surgeon or user to see or hear, and the processor can send the data to a computer and store the data in a permanent memory.

A feedback system thus may include analog indicators that are powered directly from the analog signal by amplifying a signal from piezo resistive strain gauge(s) or using the signal from piezoelectric crystal transducer(s), optionally amplified. The analog indicators may include electromechanical meters/dials, light-emitting indicators, or audible indicators, for example.

As used herein, the terms "rasp" and "roach" may be used interchangeably to refer to the same device for preparing the bone for an implant.

Figure 2:
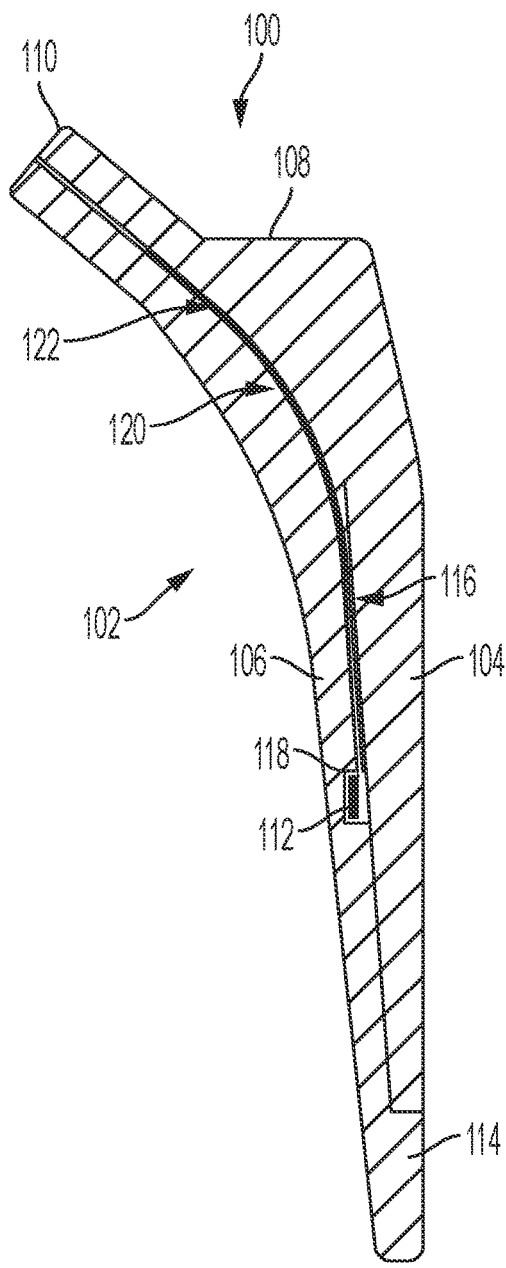
FIG. 2 illustrates a cross sectional view of the hip broach, according to an example implementation.

Referring now to the figures, FIG. 1 illustrates a side view of an example hip broach 100, according to an example implementation. FIG. 2 illustrates a cross sectional view of the hip broach 100, according to an example implementation. The hip broach 100 includes a body 102 having a first side 104, a second side 106, and a proximal portion 108, and a handle connection 110 coupled to the proximal portion 108. The hip broach 100 also includes one or more sensors 112 positioned in the body 102 between the first side 104 and the second side 106. The one or more sensors 112 detect a compression of the first side 104 toward the second side 106 and output a signal indicative of the compression.

The first side 104 and the second side 106 are coupled at a distal portion 114 of the body 102. As shown in FIGS. 1-2, the body 102 is split along a length of the body forming the first side 104 and the second side 106. For example, similar to a tuning fork, the body 102 contains a vertical split line 116 running the length of the body 102 and exiting at the distal portion 114 in the sagittal plane.

In one example, the first side 104 comprises a lateral edge of the body 102 of the hip broach 100, and the first side 104 is compressible toward the second side in a medial direction. For example, the first side 104 is free to compress in the medial direction as the force from broaching compresses the first side 104, which may be a free floating lateral edge with respect to the second side 106.

In other examples, the hip broach 100 may be configured such that the first side 104 comprises a medial edge of the body 102, and the first side 104 is compressible toward the second side 106 in a lateral direction.

In the cross sectional view in FIG. 2, the body 102 of hip broach 100 includes a cavity 118 and the one or more sensors 112 are positioned in the cavity 118. The body 102 also includes a channel 120 for one or more wire leads 122 to connect with the one or more sensors 112. In one example, as shown in FIG. 2, the one or more wire leads 122 connect the one or more sensors 112 to the handle connection 110, which is a conducting contact for connection to an impactor device (described below). In other examples, the wire leads 122 extend out of the channel 120 and exit the handle connection 110 for connection to a data acquisition and interface device.

The hip broach IN may be comprised of metal (e.g., titanium alloy, stainless steel alloy, cobalt chrome alloy), and as shown in FIG. 2, the cavity 118 creates clearance space for the one or more sensors 112. The sensor 112 may be thin in nature, and is positioned such that the sensor 112 can be compressed when the body 102 of the hip broach 100 is flexed inward. For example, when the hip broach 100 is impacted into the femur, the compression force experienced by the hip broach 100 will allow the first side 104 (e.g., the lateral edge) to compress. As the hip broach 100 is compressed, the one or more sensors 112 within the hip broach 100 that is oriented to interface with the compressional direction of the first side 104 of the hip broach 100 will relay detected and/or measured information to a data acquisition and analysis device.

The sensors 112 detect the compression of the first side 104 toward the second side 106 due to an impact applied to the proximal portion 108. In this example, the sensors 112 detect the compression via a displacement of one or more of the first side 104 and the second side 106. The one or more sensors 112 are secured to at least one of the first side 104 and the second side 106 and are in contact with the other side so that when the first side 104 and the second side 106 are compressed inward, the compression is transferred to the one or more sensors 112.

The compression that is detected can thus include deflection or displacement of one part of the body 102 of the hip broach 100 toward another part, strain in a part of the hip broach 100, or strain of a piezoelectric transducer compressed between two parts of the hip broach 100, for example. The compression detected can be a constant or dynamically changing compression (at the time of impact).

Data that is output by the sensors 112 will then be translated into a usable format that allows a surgeon to see hoop stresses being experienced in the medullary cavity, for example. The data may be provided directly without any units of force, reference to actual forces, or processing to calculate forces. In this example, the surgeon may observe data from the sensor and otherwise perform the surgery and over time and experience with the hip broach 100, can learn how to make judgments about how hard to hammer the hip broach 100.

A remote display device can be coupled to the data acquisition and analysis device, which can be an existing article of electronic hardware, or can be a proprietary display system provided with the hip broach 100. When the surgeon hammers on the impactor handle, the force generated as the hip broach 100 is impressed upon by the sides of the bone will be registered and displayed for the surgeon. This will help in assessing an amount of pressure present upon the body 102 of the hip broach 100, and as such, will also act as a guide to determine how much actual pressure and force is pressed upon the bone tissue.

As shown in FIGS. 1-2, the hip broach 100 includes the vertical split line 116 running the length of the body 102 so that the two halves (e.g., the first side 104 and the second side 106) are joined securely at the distal portion 114. The hip broach 100 may be machined from one piece of material. Thus, the first side 104, the second side 106, and the proximal portion 108 of the body 102 can be an integral component machined from one piece of material. Alternatively, the hip broach 100 can be assembled from two halves.

Figure 3:
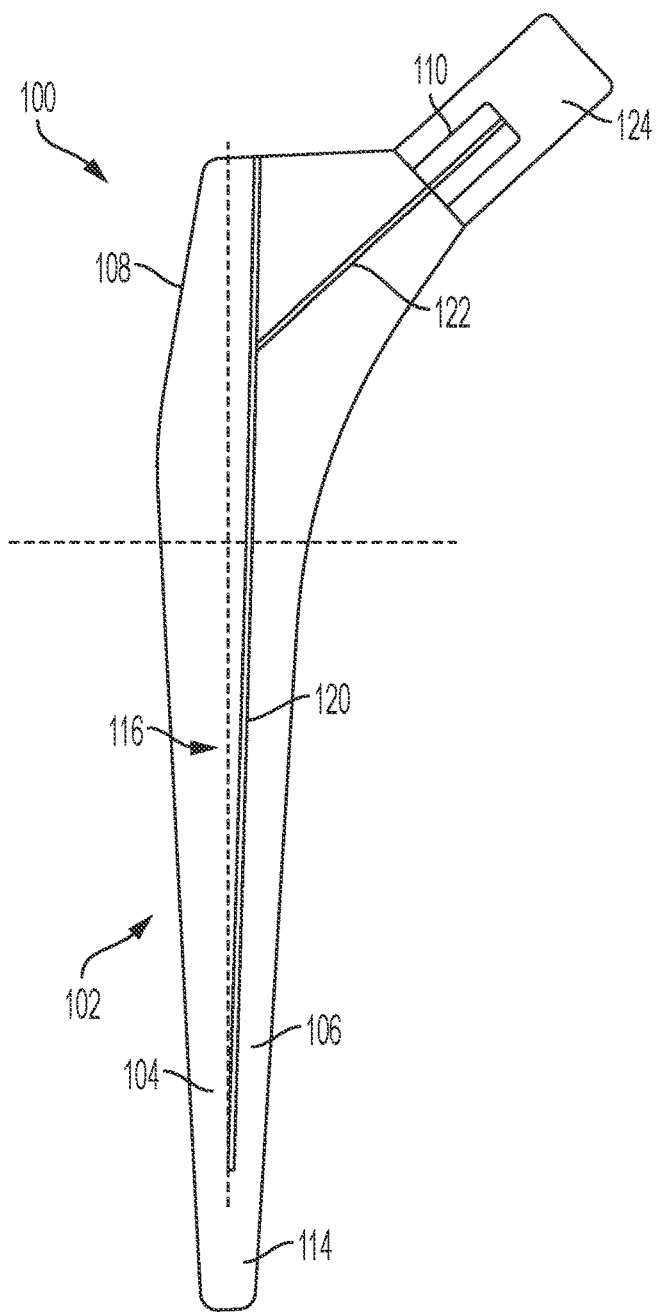
FIG. 3 illustrates another side vie the hip broach, according to an example implementation.

FIG. 3 illustrates another side view of the hip broach 100, according to an example implementation. In this example, the first side 104 and the second side 106 are only coupled at the distal portion 114 of the body 102 due to the vertical split line 116 running through the proximal portion 108 of the body 102. In addition, a portion of an impactor 124 is shown connected to the handle connection 110.

Figure 4:
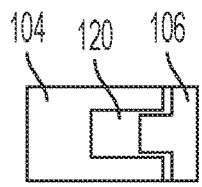
FIG. 4 illustrates a top cross sectional view of one configuration of the hip broach shown in FIG. 3, according to an example implementation.

FIG. 4 illustrates a top cross sectional view of one configuration of the hip broach 100 shown in FIG. 3, according to an example implementation. For example, the channel 120 is an exposed slot with this configuration.

Figure 5:
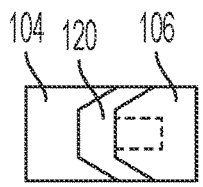
FIG. 5 illustrates a top cross sectional view of another configuration of the hip broach shown in FIG. 3, according to an example implementation.

FIG. 5 illustrates a top cross sectional view of another configuration of the hip broach 100 shown in FIG. 3, according to an example implementation. For example, here, one half of the hip broach 100 can overlap part of the other half so that the channel 120 is not open. This can help to keep debris out and not sacrifice too much area of cutting texture that is on the hip broach 100. However, the two halves will need some clearance to deflect toward each other, and therefore, any remaining gap may be left unsealed or sealed with silicone or another rubbery material, or have a gasket inserted.

Figure 6:
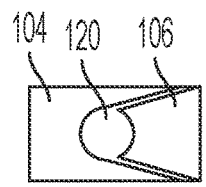
FIG. 6 illustrates a top cross sectional view of another configuration of the hip broach shown in FIG. 3, according to an example implementation.

FIG. 6 illustrates a top cross sectional view of another configuration of the hip broach 100 shown in FIG. 3, according to an example implementation. For example, in this configuration, the channel 120 is a cylindrical channel and may only be partially enclosed.

Within examples, the channel 120 provides a route for the wire lead 122 that can both provide power to the sensor 112, and receive and provide signals from and to the sensor 112. When the channel 120 extends out of the proximal portion 108 of the body 102, as shown in FIG. 3, the wire leads 122 can also extend out of the proximal portion 108 of the body 102 as well. However, as shown in FIG. 3 (and FIGS. 1-2), another route for the wire leads 122 is through the handle connection 110 to the impactor 124 by conducting contacts between the handle connection 110 and the impactor 124, and then to connect to a cable out of the impactor 124. From there, the cable from the impactor 124 can pass through a sterile-nonsterile boundary in examples where indicators are outside the sterile field. The non-sterile part of the cable can be used for all broach sizes. The sterile portion of the cable can be detachable so that a next size broach can be used. A detachment point could be at the impactor 124 and handle connection 110, mid-way along the sterile cable, or at the sterile-nonsterile boundary. Any portion of the sterile cable that is detached can be replaced with a new sterile cable with the next size broach. The cable can contain voltage source and ground wires to power the sensor 112 and any sterile-side circuitry. The same cable can contain sensor analog signal wires or digital signal wires, for example.

The sensors 112 in the hip broach 100 may be many different types or take one or many different forms. Also, one sensor or multiple sensors may be included. In one example, the one or more sensors 112 include one or more of a strain gauge, a load cell, a bending bar, an s-shaped gauge, a piezo-electric transducer, a piezo-resistive resistor, a capacitive or inductive deflection transducer to measure deflection distance, a capacitive strain sensor, or a linear variable differential transformer (LVDT) to measure deflection distance.

In one example, a strain gauge is used that is temperature-matched to the substrate material. In other examples, multiple strain gauge elements are used and arranged in a half-bridge or full-bridge configuration in order to reduce temperature-change effects on the signal. Half-bridge includes two identical gauge elements positioned in adjacent arms of one side of a Wheatstone bridge, and full-bridge includes a strain sensing element in all four arms of a Wheatstone bridge.

Furthermore, a component meant to flex or deflect, referred to as a flexure, can be secured to at least one of the first side 104 and the second side 106 and arranged to be in contact with the other half so that when the two halves are pushed inward, load is transferred to the flexure as well and it deflects. The flexure can be a load cell of a cantilever or s-shaped type. The sensors 112 can then be any kind of strain-sensing element or transducer that is bonded to a surface of the flexure substrate to measure strain.

In another example, the one or more sensors 112 include electrically conducting parallel traces that increase in resistance when subjected to a strain. For example, the sensors 112 can include transducers arranged as arms of a Wheatstone bridge circuit, and such transducers may be piezoresistive and include bonded metal foil, thin film sputter-deposited, semiconductor, or polysilicon thin film. Bonded metal foil transducers are thin metal alloy traces inset on a backing material, and can be bonded to a substrate (e.g., one of the first side 104 and the second side 106) with adhesive or epoxy in a location where strain is desired to be measured. Semiconductor gauges have traces made of silicon or germanium semiconductor. Thin film sputter-deposited gauges have a metal sputtered directly onto the substrate and then traces created by lasers.

The Wheatstone bridge circuit can also be connected to an analog to digital converter (ADC), and an amplifier can be used for the signal, such as an instrumentation amplifier, between the sensor output and the ADC. The ADC then communicates with a processor by a serial communication protocol (e.g., I²C). The processor can control a digital display or visual or audio indicators based on the strain sensor signal.

If an ADC is used, the ADC (and instrumentation amplifier) may require a reference voltage that can be supplied by a shunt diode with current limited to its ideal operating current. A buffer operational amplifier can be used between the reference voltage source and the ADC or amplifier reference voltage pin.

In still further examples, the sensor 112 can include a fiber optic strain gauge with a Fiber Bragg Grating segment welded to the flexure. The sensing circuit can then detect change in frequency of light waves that are being reflected by the Bragg grating.

Figure 7:
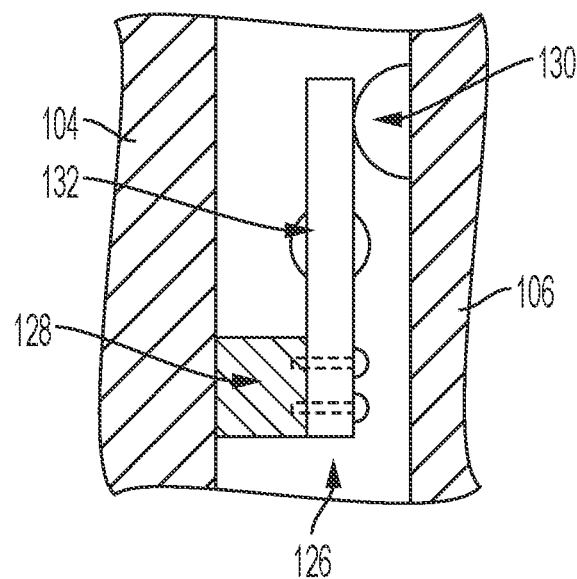
FIG. 7 illustrates a side view of an example sensor configuration for the hip broach, according to an example implementation.
Figure 8:
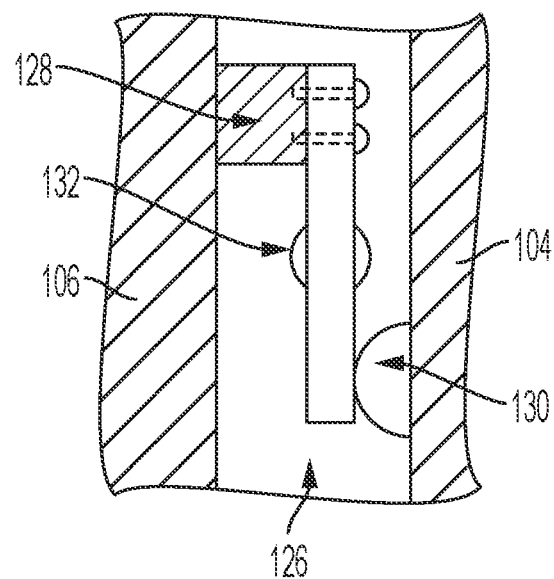
FIG. 8 illustrates a side view of another example sensor configuration for the hip broach, according to an example implementation.
Figure 9:
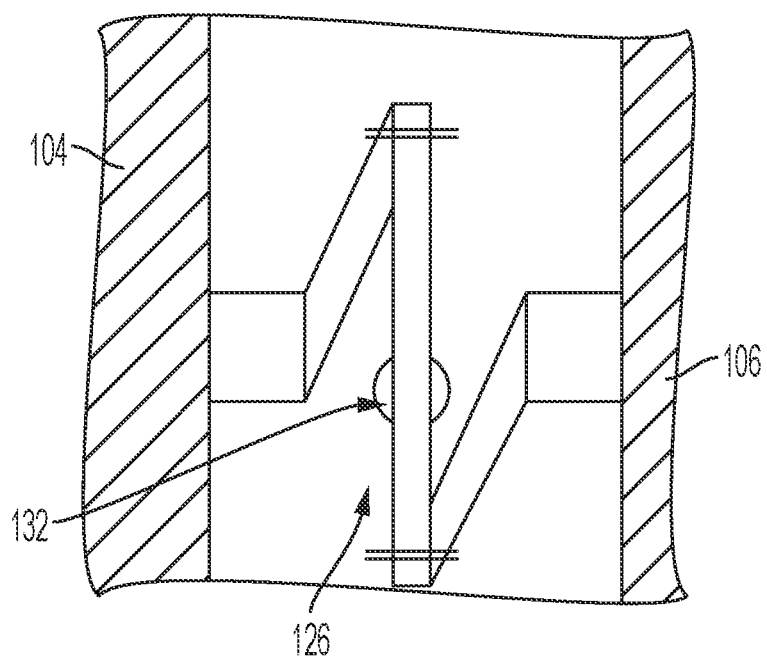
FIG. 9 illustrates a side view of another example sensor configuration for the hip broach, according to an example implementation.

FIGS. 7-9 illustrate side views of example sensor configurations for the hip broach 100, according to an example implementation. FIG. 7 illustrates a flexing structure 126 mounted in the cavity 118, or the flexing structure 126 can be mounted inside the sensor 112 as well. In the example shown in FIG. 7, the flexing structure 126 is arranged as a bending-bar cantilever type sensor that makes contact between the first side 104 and the second side 106 of the body 102. The flexing structure 126 is fastened to the first side 104 through a base 128 and in floating contact with the second side 106 at a contact 130.

FIG. 8 illustrates the flexing structure 126 arranged in an opposite manner as shown in FIG. 7, in which the flexing structure 126 is fastened to the second side 106 through the base 128 and in floating contact with the first side 104 at the contact 130.

FIG. 9 illustrates another configuration of the flexing structure 126 arranged as an S-shaped configuration, and the flexing structure 126 is fastened to both the first side 104 and the second side 106, and the first side 104 and the second side 106 push inward on the flexing structure 126 at substantially the same position. This configuration can also include an S-beam type load cell, for example.

In FIGS. 7-9, the flexing structure 126 is shown with a strain transducer 132 mounted thereon, which may be any type of transducer described, such as piezoresistive type or optical fiber Bragg grating. The strain transducer 132 may be positioned on one side of the flexing structure 126 or on both sides.

Within any examples described herein, the sensor 112 may include the flexing structure 126, or a flexing structure 126 can be used with additional sensors to detect the compression of the body 102 of the hip broach 100.

Figure 10:
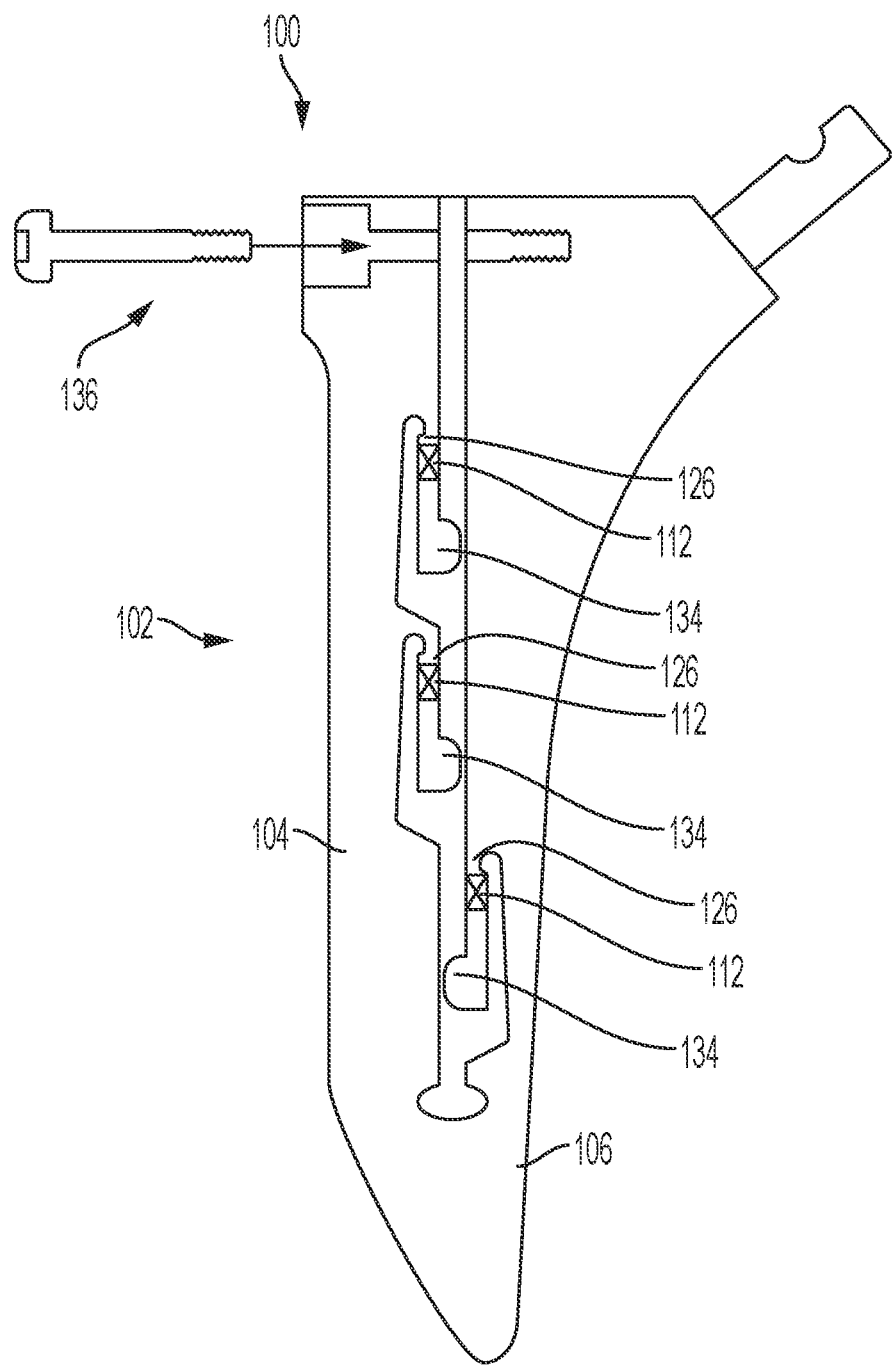
FIG. 10 illustrates a side view of an example cantilever load cell sensor included in the body of the hip broach, according to an example implementation.

FIG. 10 is a side view of an example cantilever load cell sensor 112 included in the body 102 of the hip broach 100, according to an example implementation. In this example, one or more of the flexing structure 126 is made integral to the body 102 of the hip broach that bridge a gap or gaps between the first side 104 and the second side 106 of the two halves. A contacting pad 134 is positioned at one end of each flexing structure 126 to transfer load from the first side 104 to the second side 106. The other end of the flexing structure 126 is attached to the second side 106. Then, sensors 112 or sensing components, such as strain transducers, are bonded to the flexing structure 126. For example, piezoresistive transducers (e.g., strain gauges) can be bonded to the flexing structure 126 on either side of the flexing structure 126.

FIG. 10 also illustrates a pre-load bolt 136 near the top of the hip broach 100 to pull the first side 104 and the second side 106 together so that a neutral position of the sensor 112 and flexing structure 126 can be slightly loaded in order to have a stable output signal and ensure that the flexing structure 126 makes contact with the first side 104. The pre-load bolt 136 is passed through an unthreaded hole in the first side 104 and into a threaded hole in the second side 106, and then a head of the pre-load bolt 136 contacts the first side 104 to pull the first side 105 toward the second side 106.

Figure 11:
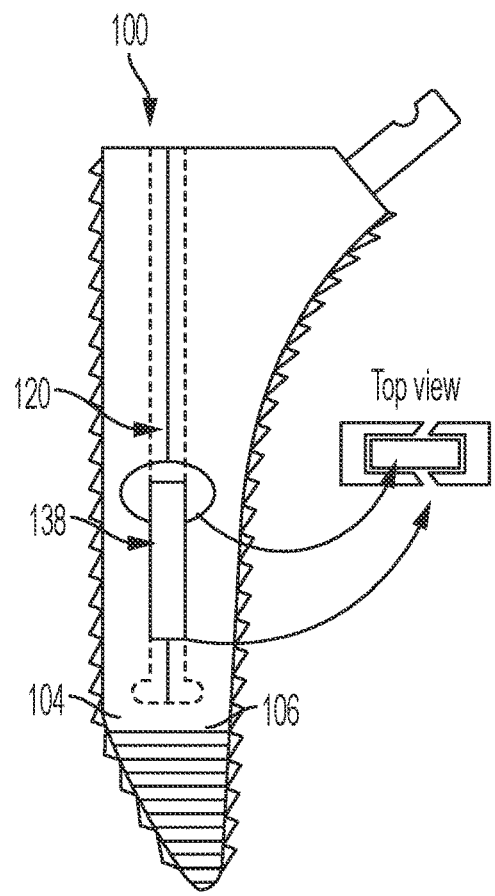
FIG. 11 illustrates a side view of an example of the hip broach with a sensor module inserted into the channel from the top, according to an example implementation.

FIG. 11 illustrates a side view of an example of the hip broach 100 with a sensor module 138 inserted into the channel 120 from the top, according to an example implementation. The sensor module 138 can have sensors positioned across a gap to detect deflection of the first side 104 and the second side 106 inward toward each other. The sensor module 138 can be inserted at the time of surgery. In this example, the sensor module 138 and the body 102 can be sterilized separately. The sensor module 138 may be plastic or metal (such as aluminum), for example.

Figure 12:
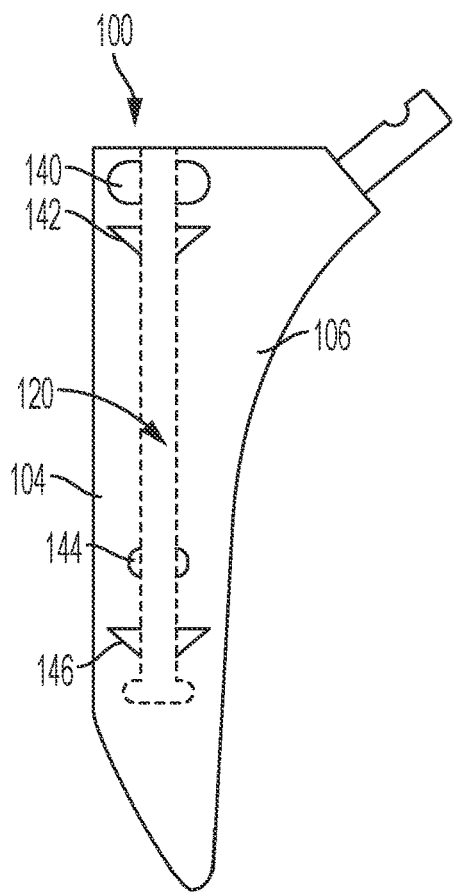
FIG. 12 illustrates a side view of another example of the hip broach, according to an example implementation.

FIG. 12 illustrates a side view of another example of the hip broach 100, according to an example implementation. The channel includes detents 140, 142, 144, and 146, and the sensor module 138, that can match to corresponding bumps or tabs on the sensor module 138 to lock the sensor module 138 into place. The channel 120 may include a lip at the top that makes the opening slightly narrower and prevents the sensor module 138 from sliding out once inserted.

Figure 13:
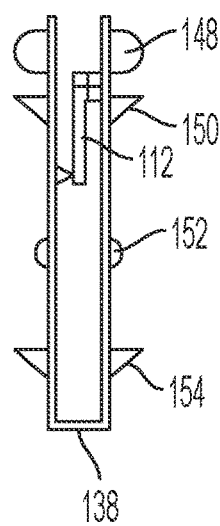
FIG. 13 illustrates a side view of an example of the senor module, according to an example implementation.

FIG. 13 illustrates a side view of an example of the senor module 138, according to an example implementation. The sensor module 138 includes bumps or tabs 148, 150, 152, 154 on an exterior surface that snap into place in the detents 140, 142, 144, and 146 of the channel 120. The outer walls of the sensor module 138 are seated against the channel 120 walls so that load is transferred to the sensor module and the sensor(s) 112 therein.

Figure 14:
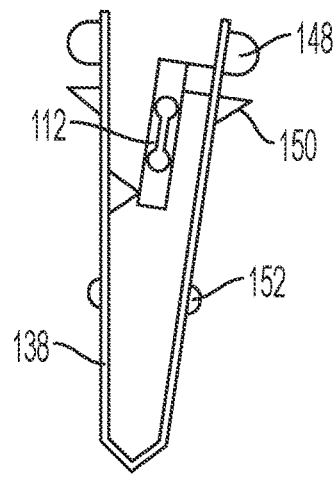
FIG. 14 illustrates a side view of another example of the sensor module, according to an example implementation.

FIG. 14 illustrates a side view of another example of the sensor module 138, according to an example implementation. The sensor module 138 is shown to have walls slightly off-parallel, as shown in FIG. 14, and the channel 120 may have walls that are closer to parallel so that the sensor module 138 will flex when inserted, pressing the sensor module 138 flush against the channel 120 and pre-loading the sensors, for example.

As shown and described above, the sensors 112 can be positioned in the body 102 of the hip broach 100, and additional electronics (e.g., ADC and processor) can be positioned external (in non-sterile region).

In other examples, the sensor 112 and the additional electronics (e.g., ADC circuit and processor) may be positioned in the body 102 of the hip broach 100. For example, one or more processors can be positioned in the body 102, and may be coupled to the one or more sensors 112 to receive the output signals and to process the output signals into information indicative of a force transferred to a bone for output to a display device. Moreover, in further examples, a tireless transmitter can be positioned in the body 102 and coupled to the one or more sensors 112 to wirelessly transmit the signal to an external computing device.

Thus, the processor can be positioned in the hip broach 100 or external to the hip broach 100, such as within a computing device remote from the hip broach 100.

Figure 15:
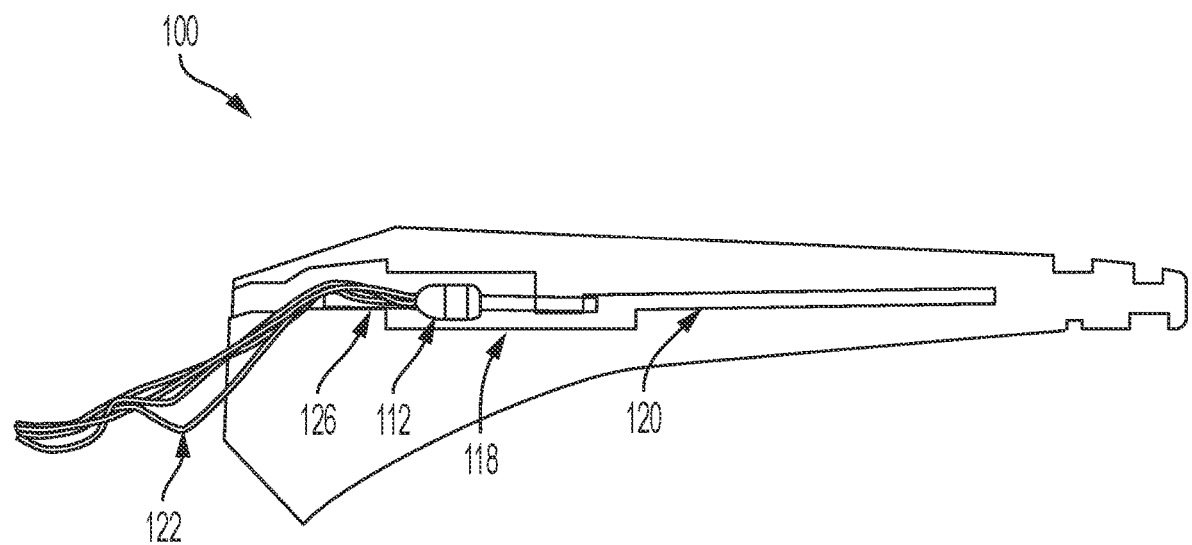
FIG. 15 illustrates a side view of another example of the hip broach, according to an example implementation.
Figure 16:
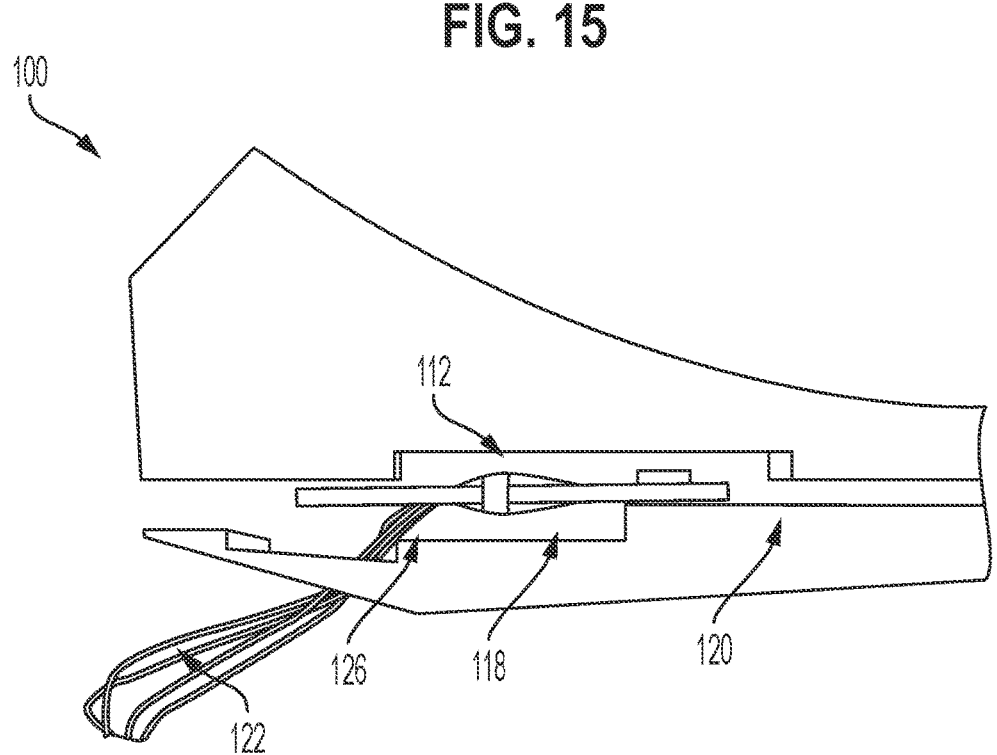
FIG. 16 illustrates an alternate side view of the hip broach shown in FIG. 15, according to an example implementation.

FIG. 15 illustrates a side view of another example of the hip broach 100, according to an example implementation. FIG. 16 illustrates an alternate side view of the hip broach shown in FIG. 15, according to an example implementation. In FIGS. 15-16, the hip broach 100 is a plastic 3D printed device including a bending bar load cell type flexing structure 126 with the sensor 112 mounted in the cavity 118.

In these examples, the flexing structure 126 and the sensor 112 may be considered the sensor positioned inside the hip broach 100, such that both components together are used to detect the compression. In other examples, the sensor 112 includes internal flexing structures inherent in the sensing mechanism.

Figure 17:
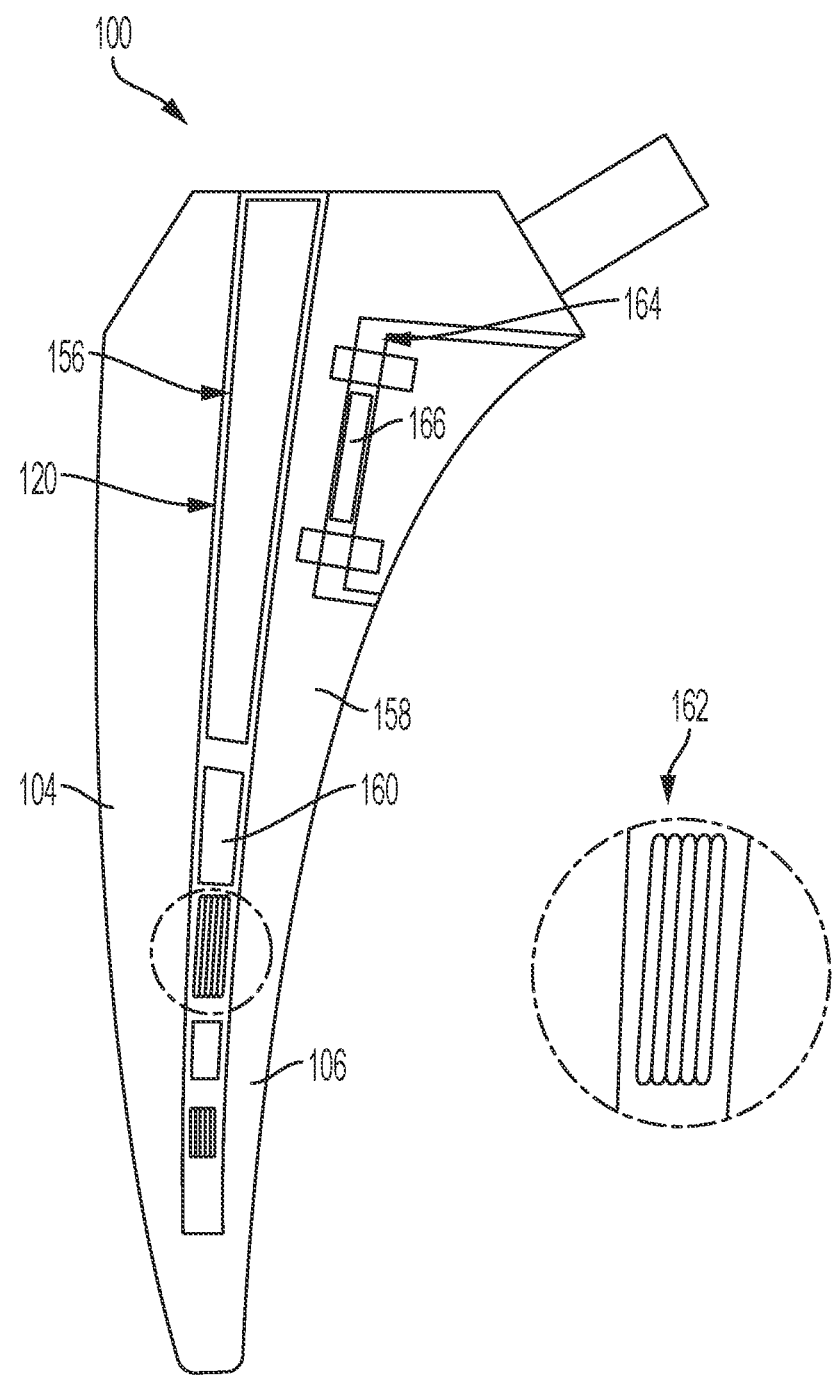
FIG. 17 illustrates a side view of another example of the hip broach, according to an example implementation.

FIG. 17 illustrates a side view of another example of the hip broach 100, according to an example implementation. In FIG. 17, multiple piezoelectric transducers 156, 158, and 160 are positioned in the channel 120, for example. More or fewer transducers may be included. In addition, a stacked set 162 of multiple thinner transducers may be included. The piezoelectric transducers include thin metal electrodes at either end of their compression active direction and may include an insulator layer between each electrode and the broach material and between the electrodes of separate transducers. The transducers can be snugly fit between the first side 104 and the second side 106, such as through the use of a pre-load bolt/screw, for example.

Also shown in FIG. 17 is a second channel 164 positioned in the body 102 of the hip broach 100, and another transducer 166 can be positioned in the second channel 164 to detect compression in the proximal portion of the hip broach, for example.

Figure 18:
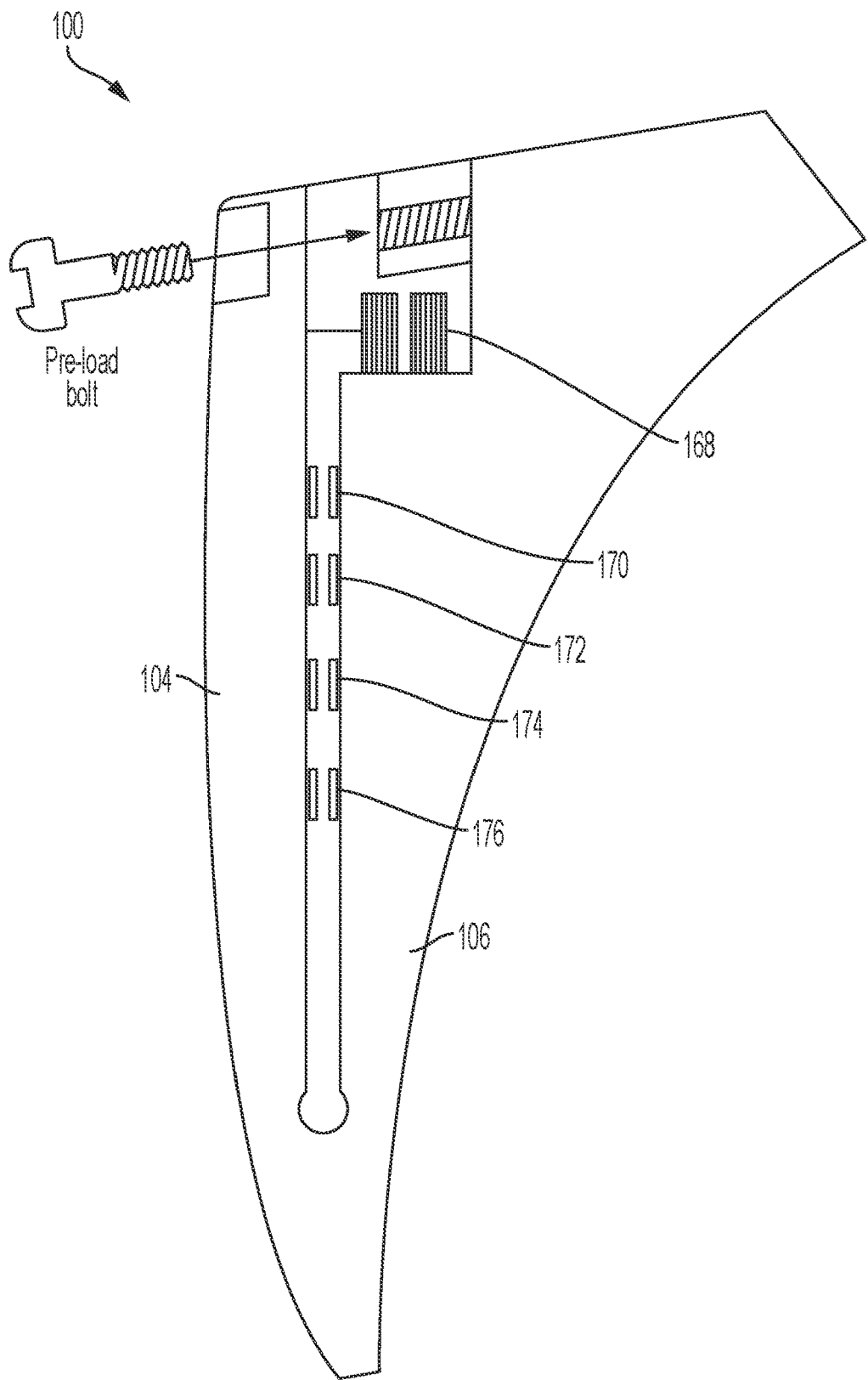
FIG. 18 illustrates a side view of another example of the hip broach, according to an example implementation.

FIG. 18 illustrates a side view of another example of the hip broach 100, according to an example implementation. In FIG. 18, examples of non-contact deflection/displacement sensors are shown. For example, a type of linear motion transducer can be used such as an LVDT (linear variable differential transformer), or capacitance sensors 170, 172, 174, and 176 could also detect deflection.

Figure 19:
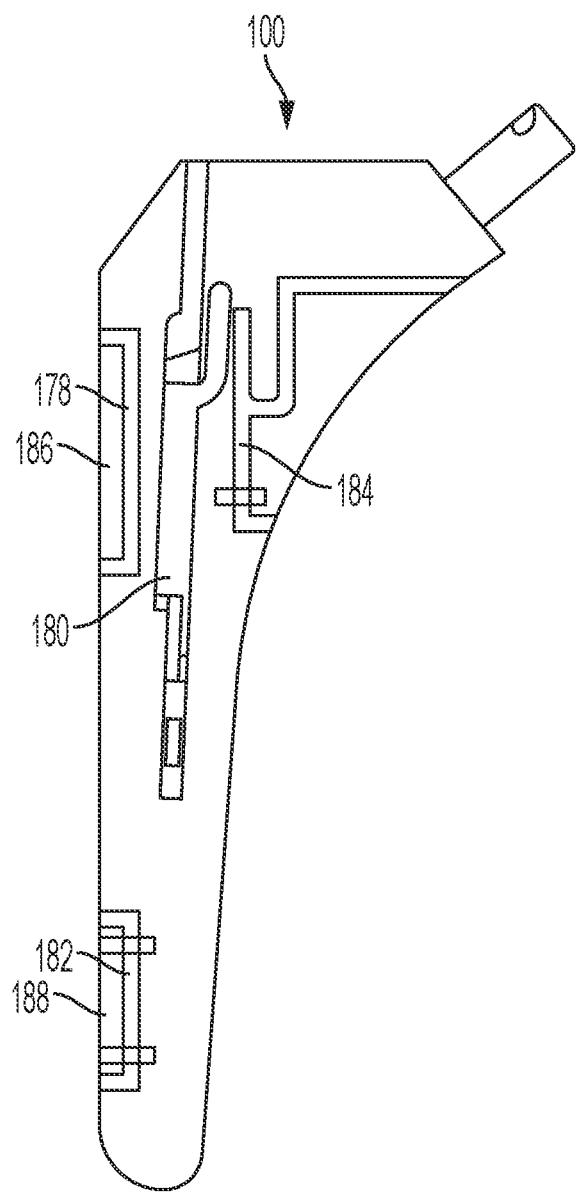
FIG. 19 illustrates a side view of another example of the hip broach, according to an example implementation.

FIG. 19 illustrates a side view of another example of the hip broach 100, according to an example implementation. In FIG. 19, examples are shown for various splits/gaps/slots positioned in the body 102 of the hip broach 100. Many examples above illustrate a center split or center channel. In the example shown in FIG. 19, one or more additional channels 178, 180, 182, and 184 may be included, and sensors or sensor modules may be inserted or positioned in any of these channels. With respect to the channels 178 and 182, plates 186 and 188 can be separate components that engage with the body 102 of the hip broach 100 through screws, for example.

Figure 20:
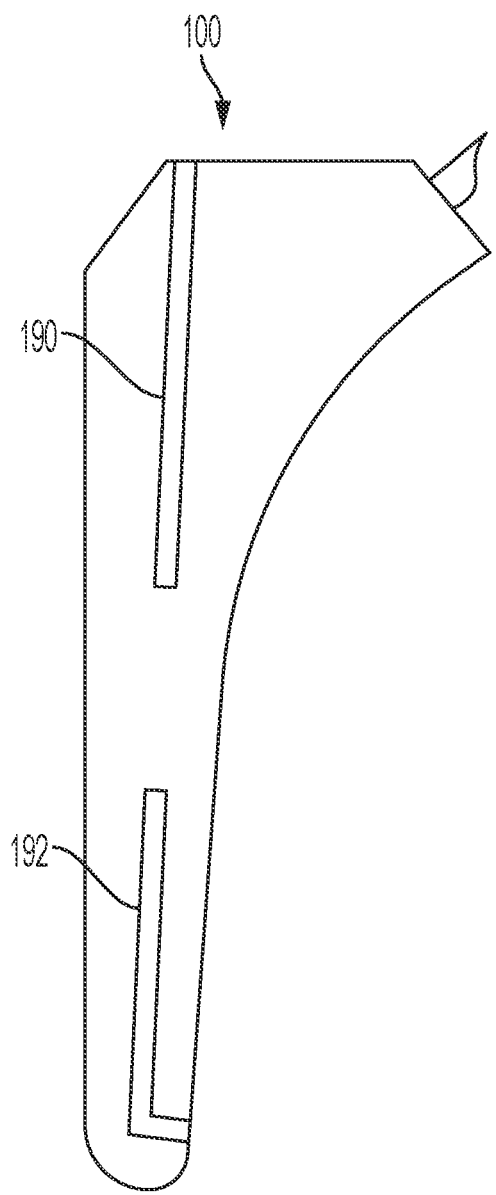
FIG. 20 illustrates a side view of another example of the hip broach, according to an example implementation.

FIG. 20 illustrates a side view of another example of the hip broach 100, according to an example implementation. In FIG. 20, two alternate channels 190 and 192 are shown in which sensors or sensor modules may be inserted or positioned, for example.

Figure 23:
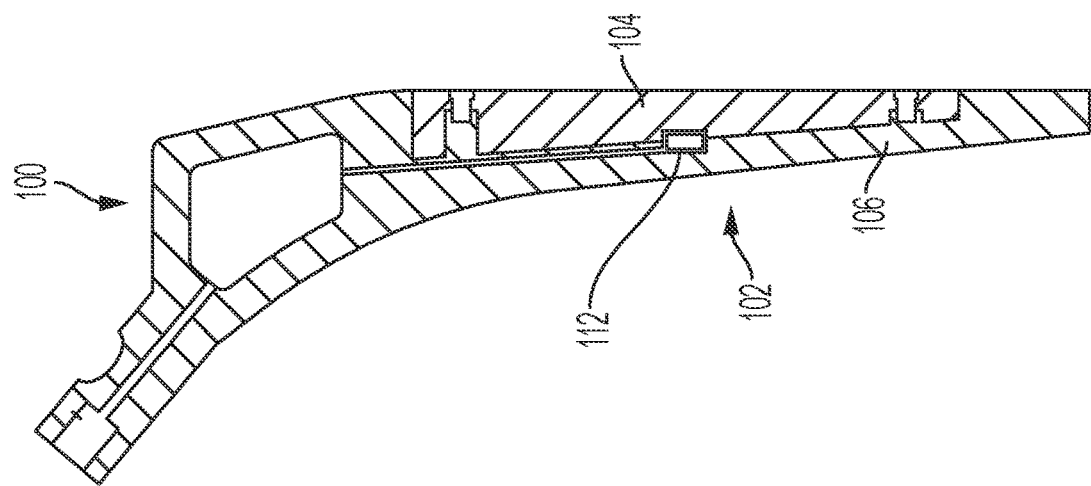
FIG. 23 illustrates a cross sectional view of the hip broach of FIG. 21, according to example implementation.
Figure 22:
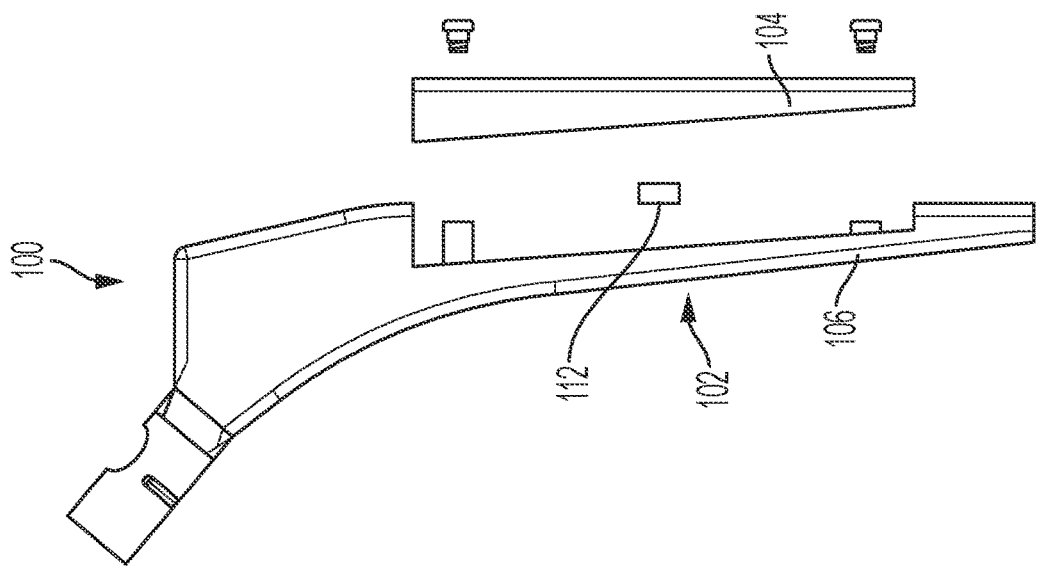
FIG. 22 illustrates a side view of the hip broach of FIG. 21, according to example implementation.
Figure 21:
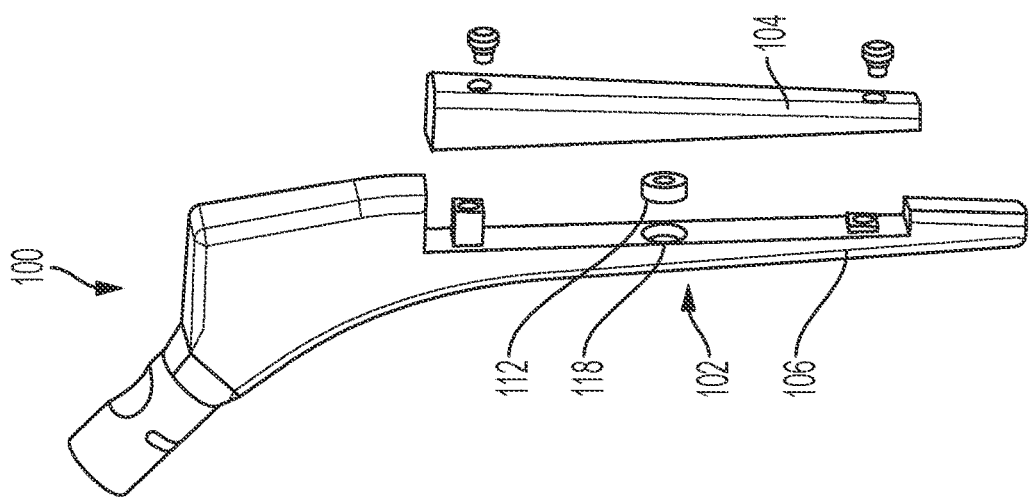
FIG. 21 illustrates a side dimensional view of a further example of the hip broach, according to example implementation.

FIGS. 21-23 illustrate side views of further examples of the hip broach, according to example implementations. FIG. 21 illustrates a side dimensional view of the hip broach 100 with a detachable portion, FIG. 22 illustrates a side view of the hip broach 100 of FIG. 21, and FIG. 23 illustrates a cross sectional view of the hip broach 100 of FIG. 21.

In FIG. 21, one section of the hip broach 100 is a separate component that engages with the body 102 of the hip broach 100 with at least one or more slot screw, peg, or smooth shank screw. For example, the first side 104 is a separate component that engages with the body 102 with at least one or more of a screw and a peg. The one or more sensors 112 can be placed in between the two separate halves. In this example, the free section of the hip broach 100 (e.g., the first side 104) is thick enough to allow for linear compressional translation as the first side 104 is being impacted into the femur without sections of the first side 104 to warp or bend in an uneven fashion. This may enable the surgeon to know a single force being experienced on a single line of axis, and the data output from the sensor 112 can be displayed via auditory or simple visual interface.

In FIG. 23, the sensor 112 is positioned in the cavity 118 that allows for all necessary electronics and programmable computers needed to be housed in the hip broach 100 as well. In the example where all electronics are positioned inside the hip broach 100, all data may be transmitted via wireless connection (e.g., Bluetooth communications), or other wireless methods to a user interface.

Figure 24:
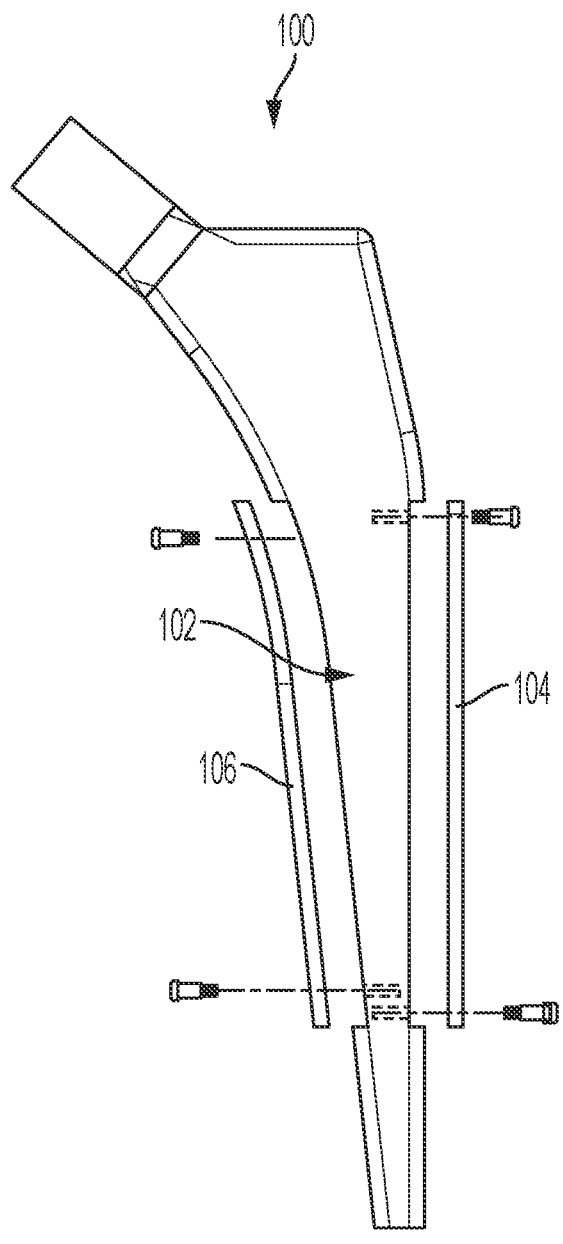
FIG. 24 illustrates a side view of the hip broach with detachable portions, according to an example implementation.
Figure 25:
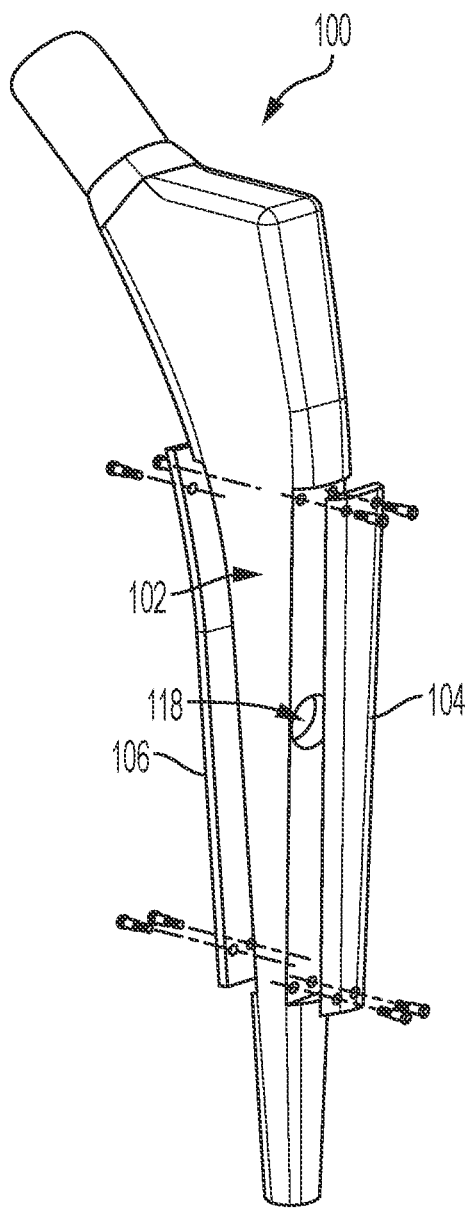
FIG. 25 illustrates a side dimensional view of the hip broach of FIG. 24, according to an example implementation.

FIGS. 24-25 illustrate side views of further examples of the hip broach, according to example implementations. FIG. 24 illustrates a side view of the hip broach 100 with detachable portions, and FIG. 25 illustrates a side dimensional view of the hip broach 100 of FIG. 24. In these examples, the first side 104 and the second side 106 are separate components that engage with the body 102. Thus, the first side 104 and the second side 106 are movable relative to the body 102. More or fewer plates and sensors can be used with the body 102 than as shown, for example. In FIGS. 24-25, the cavity 118 allows for a load cell to be placed in the body 102 of the hip broach 100. The medial plate and the lateral plate (e.g., the first side 104 and the second side 106) can then be fixed by smooth shank screws, or other types of screws. The smooth shank screws will assure that all the compressional forces transmitted onto the plates will be relayed to the sub-miniature load cells.

Figure 26:
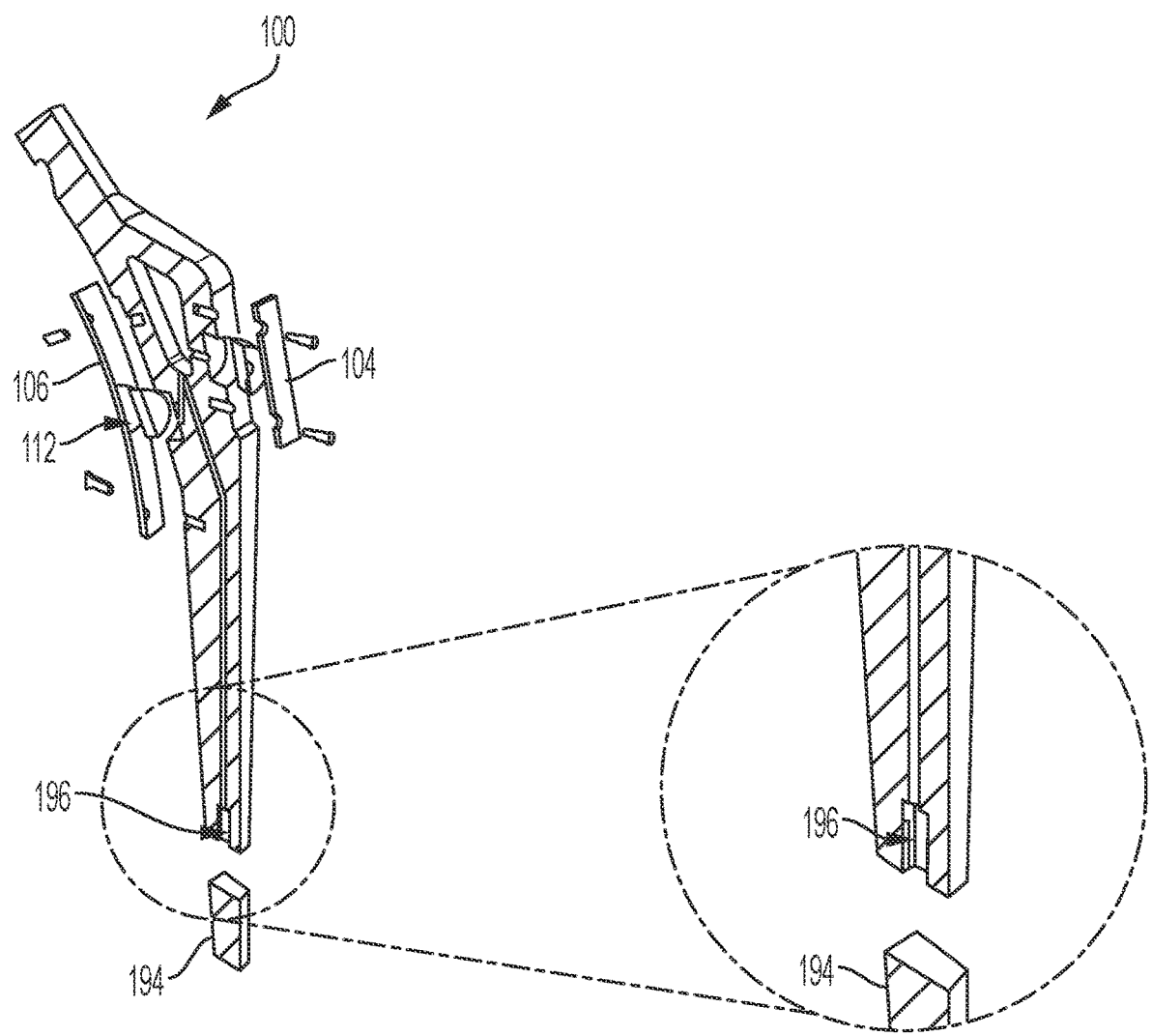
FIG. 26 illustrates a side cross sectional view of another example of the hip broach, according to an example implementation.

FIG. 26 illustrates a side cross sectional view of another example of the hip broach, according to an example implementation. In this example, a distal sensor 194 is positioned at a distal tip portion of the body 102 to detect a deflection of the distal tip portion of the body 102. Specifically, the distal sensor 194 is positioned within a cavity 196 of the distal tip portion of the body 102 and seals the cavity 196. In the distal end of the hip broach 100, a strain gauge can be placed inside the distal cavity that will measure the forces at distal stem tip of the hip broach 100. The main wire channel will allow wires to run through the hip broach 100 to connect to all the sensors. The hip broach 100 will not be limited to a specific number of each type of sensor. There maybe be more load cells and strain gauges used to increase the effectiveness of the sensor feedback broach system.

Figure 27:
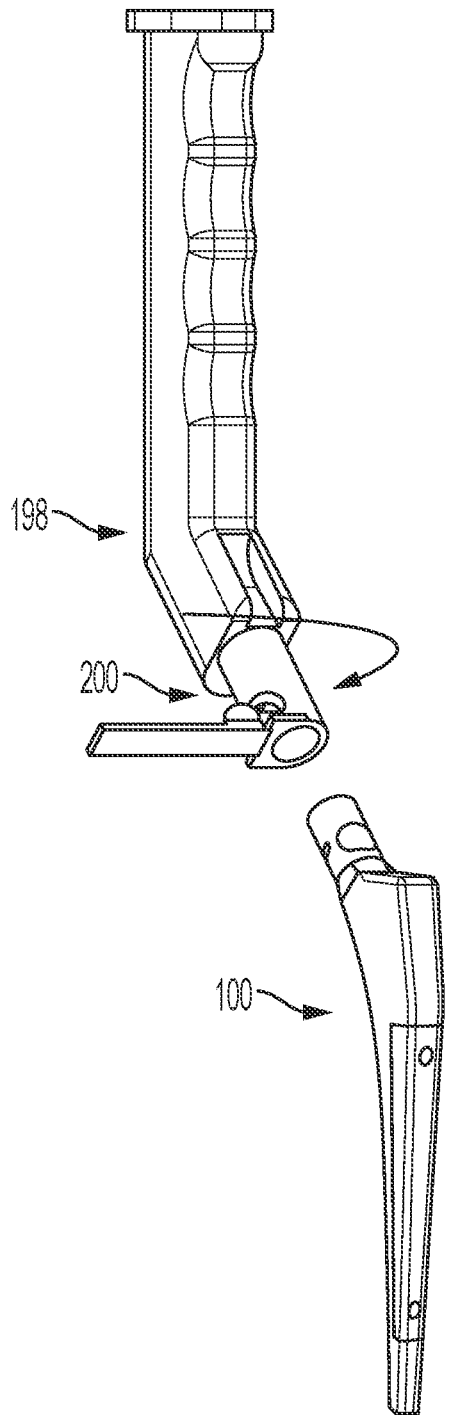
FIG. 27 illustrates a side view of an example of the hip broach being attached to an impactor handle, according to an example implementation.
Figure 28:
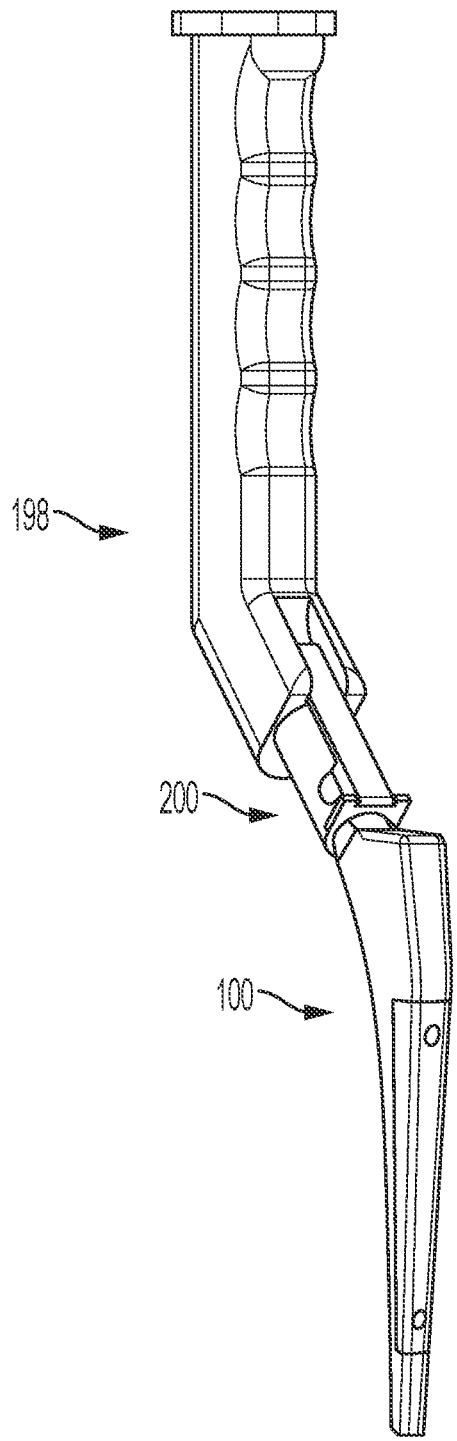
FIG. 28 illustrates a side view of the hip broach attached to an impactor handle according to an example implementation.

FIG. 27 illustrates a side view of an example of the hip broach 100 being attached to an impactor handle 198, according to an example implementation. FIG. 28 illustrates a side view of the hip broach 100 attached to an impactor handle 198, according to an example implementation. The impactor handle 198 includes a rotating cam lock mechanism 200. A bottom of the impactor handle 198 will engage the hip broach 100 with a semi-dome spherical indent on the inside to guide the connection. The connecting component of the impactor handle 198 will then be rotated 90° to position the cam latch for engagement. Once the cam is engaged, the hip broach 100 will be securely fitted to the impactor handle 198, as shown in FIG. 28.

Figure 29:
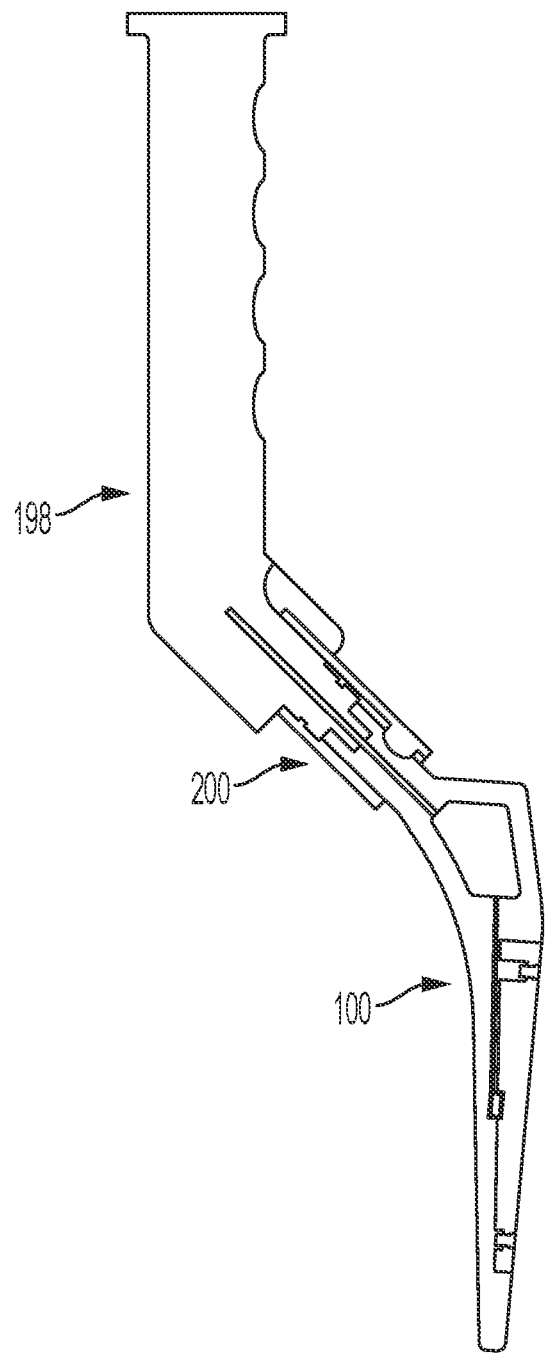
FIG. 29 illustrates a cross sectional view of the hip broach connected to the impactor handle, according to an example implementation.

FIG. 29 illustrates a cross sectional view of the hip broach 100 connected to the impactor handle 198, according to an example implementation. The impactor handle 198 and the hip broach 100 have channels that connect wire leads with one another. The impactor handle 198 has the ability to house the electronics and internal power supply needed to power all necessary components (e.g., sensors and processors) of the hip broach 100, for example.

Figure 30:
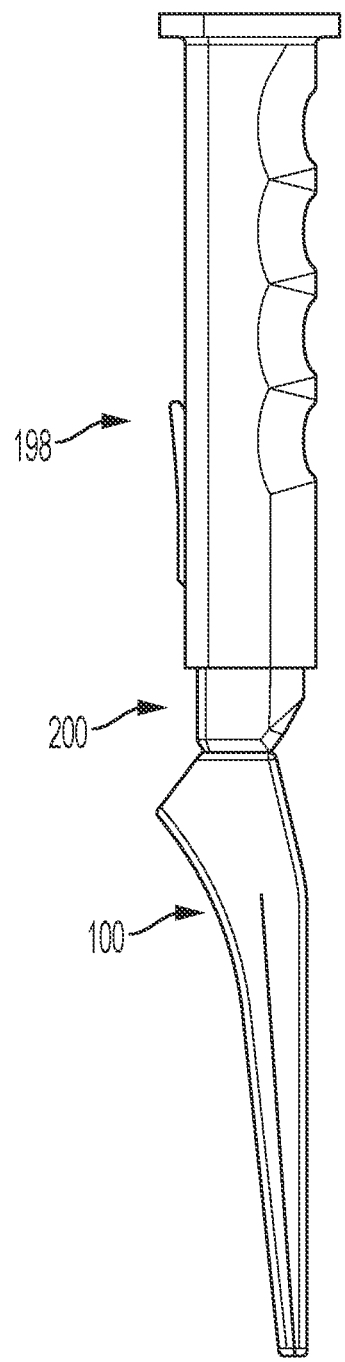
FIG. 30 illustrates a side view of the hip broach connected to the impactor handle in which the impactor handle attaches in the same axis as a length of hip broach, according to an example implementation.

FIG. 30 illustrates a side view of the hip broach 100 connected to the impactor handle 198 in which the impactor handle 198 attaches in the same axis as a length of hip broach 100, according to an example implementation. The hip broach 100 can be wireless or wired. In the wired embodiment, the hip broach 100 features an electrical component that is located proximally in a housing cavity, and the electrical component that is embedded in the hip broach 100 connects to an electrical connection through the impactor handle 198 to power and communicate with the sensors within the hip broach 100. The electrical wires are not limited to running through the hip broach/impactor handle connection. In the wireless embodiment, a programmable computer/microcontroller will be housed in the main cavity of the hip broach 100. This programmable computer/microcontroller will collect the analog data from the subminiature load cells, and transmit the data digitally to a user interface that may be a computer or display. The sub-miniature load cells will receive direct input from the forces experienced by the hip broach.

Figure 31:
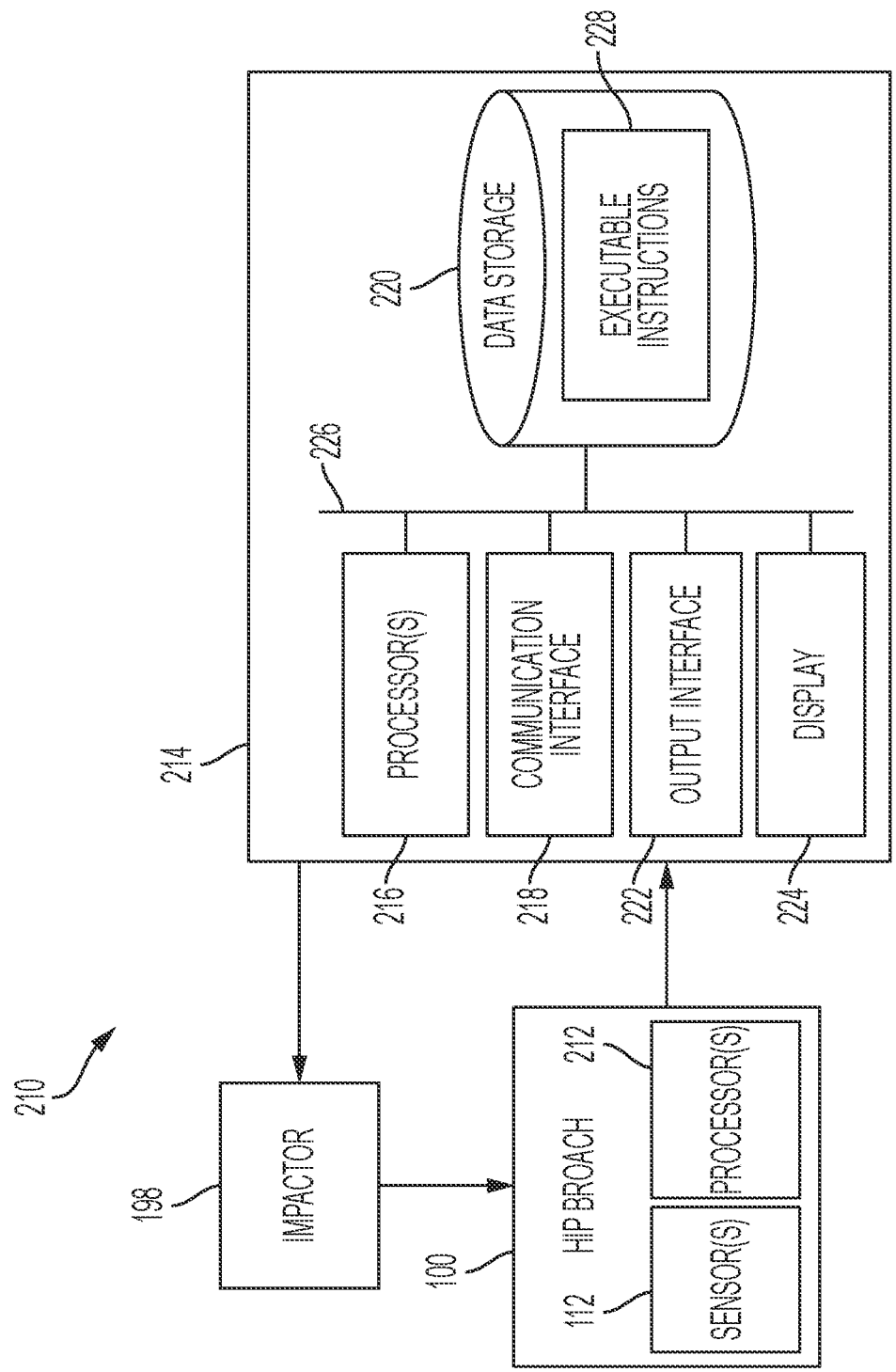
FIG. 31 is a block diagram illustrating an example system, according to an example implementation.

FIG. 31 is a block diagram illustrating an example system 210, according to an example implementation. The system 210 includes the hip broach 100 shown to include the sensors 112 and one or more processor(s) 212 that connects to a computing device 214. The computing device 214 may connect to the impactor 198 to control operations of the impactor 198.

The computing device 214 has a processor(s) 216, and also a communication interface 218, data storage 220, an output interface 222, and a display 224 each connected to a communication bus 226. The computing device 214 may also include hardware to enable communication within the computing device 214 and between the computing device 214 and other devices (not shown). The hardware may include transmitters, receivers, and antennas, for example.

The communication interface 218 may be a wireless interface and/or one or more wireline interfaces that allow for both short-range communication and long-range communication to one or more networks or to one or more remote devices. Such wireless interfaces may provide for communication under one or more wireless communication protocols, such as Bluetooth or WiFi (e.g., an institute of electrical and electronic engineers (IEEE) 802.11 protocol), or near-field communication (NFC), and/or other wireless communication protocols. Thus, the communication interface 218 may be configured to receive input data from the sensors 112 and/or the processor(s) 212, and may also be configured to send output data to other devices.

The communication interface 218 may also include a user-input device, such as a keyboard or mouse, for example.

The data storage 220 may include or take the form of one or more computer-readable storage media that can be read or accessed by the processor(s) 216. The computer-readable storage media can include volatile and/or non-volatile storage components, such as optical, magnetic, organic or other memory or disc storage, which can be integrated in whole or in part with the processor(s) 216. The data storage 220 is considered non-transitory computer readable media. In some examples, the data storage 220 can be implemented using a single physical device (e.g., one optical, magnetic, organic or other memory or disc storage unit), while in other examples, the data storage 220 can be implemented using two or more physical devices.

The data storage 220 thus is a non-transitory computer readable storage medium, and executable instructions 228 are stored thereon. The instructions 228 include computer executable code. When the instructions 182 are executed by the processor(s) 216, the processor(s) 216 are caused to perform functions. Such functions include causing operation of the impactor 198 based on a feedback loop of data received from the hip broach 100, for example.

The processor(s) 216 may be a general-purpose processor or a special purpose processor (e.g., digital signal processors, application specific integrated circuits, etc.). The processor(s) 216 may receive inputs from the communication interface 218, and process the inputs to generate outputs that are stored in the data storage 220 and output to the display 224. The processor(s) 216 can be configured to execute the executable instructions 228 (e.g., computer-readable program instructions) that are stored in the data storage 220 and are executable to provide the functionality of the computing device 214 described herein.

The output interface 222 outputs information to the display 224 or to other components as well. Thus, the output interface 222 may be similar to the communication interface 218 and can be a wireless interface (e.g., transmitter) or a wired interface as well. The output interface 222 may send information about the determined forces caused by broaching to the display 224 for viewing by the surgeon during surgery.

In one example use of the system 210, the hip broach 100 is attached to the impactor 198 to apply the force for impacting the hip broach 100 into the bone, and the one or more processors 212 output data signals to control the impactor 198 based on the determined force transferred to the bone. The one or more processors 212 apply a feedback loop to the impactor 198 to prevent further broaching based on the determined force transferred to the bone being above a threshold amount. The one or more processors 212 output an audible or visual signal to a display interface based on the determined force transferred to the bone being above a threshold amount.

Figure 32:
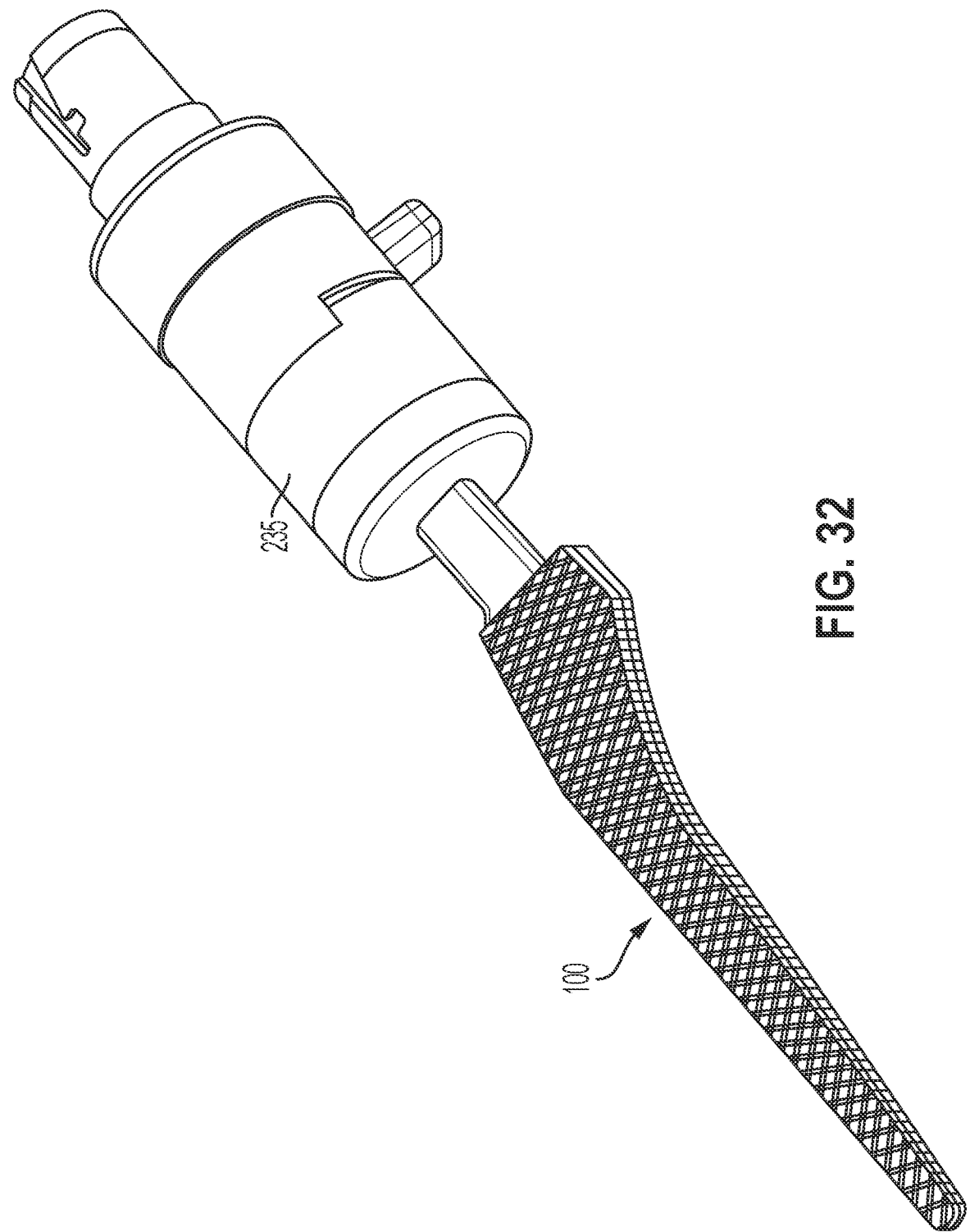
FIG. 32 illustrates an example powered reciprocating rasp device connected to the hip broach, according to an example embodiment.

FIG. 32 illustrates an example powered reciprocating rasp device 235 connected to the hip broach 100, according to an example embodiment. The feedback loop may be used as a method of feedback for powering the powered reciprocating rasp device 235 that drives the hip broach 100 into the bone. The feedback loop can cause additional or less power to be applied by the powered reciprocating rasp device 235, for example, based on outputs of the sensor(s) 112 in the hip broach 100.

Referring to FIG. 31, the surgeon, or the surgical staff, can refer to the display 224 or output interface 222 to gauge the forces present upon the hip broach 100. The display 224 or output interface 222 can be audio, audio-visual, visual, or any other type of output that can provide the surgeon with real time feedback that is indicative of the forces experienced during initial impaction. The forces will be a reflection of the forces present inside the bone tissue or medullary cavity. These forces can be monitored to prevent the surgeon from fracturing the metaphyseal and diaphyseal portion of the femur which is the bone tissue that experiences the greatest hoop stresses when the hip broach 100 is being impacted. The forces will also be derived from the proximal region of the femur as the hip is being broached. The monitoring is done by observing the display 224 that is linked via wire or wirelessly to the hip broach 100. To prevent femoral fracture from occurring, the feedback loop is present to prevent further broaching.

In one example, the hip broach 100 includes multiple sensors and the force is mapped along the length of the hip broach 100 to identify an area along which the forces are being experienced. This may include measuring forces in regions and forces in other regions due to the multiple sensors. Outputs of the multiple sensors can be displayed to illustrate specific regions where the stress is being experiencing on the hip broach 100 so that the surgeon can discontinue broaching if the hoop stresses in a region of the proximal femur becomes too large. In another example, a predetermined force threshold can be set by the surgeon before broaching begins so that when the hip broach 100 experiences the force that was preset by the surgeon, an audible or visual signal through the display 224 can be given to the surgeon to stop broaching or to change the hip broach 100 to a different size to prevent femoral failure from occurring due to overloading in hoop stress. The bone at the metaphyseal and diaphyseal region of the femur is most susceptible to fracture at the hands of inexperienced surgeons if the hoop stress is too large when the femur is being broached.

An example hip replacement surgical method using the hip broach 100 and feedback system is described below. First, the patient is prepped for the hip replacement surgery in a manner that is traditional for this type of undertaking, using any of the incisional approaches appropriate for hip replacement surgery. The surgeon creates an incision through the dermal and subcutaneous tissue, incises the joint capsule of the hip, and exposed the joint surfaces. Once the joint is exposed and the hip joint disarticulated (separated), the surgeon can begin making cuts upon the bone tissue. Following resection of the femoral neck and removal of the arthritic hip ball (femoral head) with an oscillating saw, the acetabulum is prepared in the usual manner for insertion of the femoral acetabular (cup) prosthesis.

Once the acetabular component is implanted, the surgeon prepares the proximal femur with a box chisel, a punch hammered a few millimeters into the femoral canal to create a "starter" path for the "broaching" in which sequentially larger broaches are hammered down the canal to prepare the bone of the proximal femur for insertion of the final femoral prosthetic component. Thus, the femoral cavity is manually prepared with broaches of incremental increasing size impacted into the femur with a hand mallet and impactor instrument that attaches to the proximal end of each broach. This activity is called "broaching" the femur. Optionally a rod can be impacted through the area to be broached and into the intramedullary canal of the femur to further prepare the canal, and then the rod is removed.

The broaching procedure thus includes impacting an initial size broach, containing a sensor(s) as described above into the proximal femur. At least one data point is recorded as derived from the signal produced by any sensor/transducer within the broach. The data could be recorded by an automated measurement or feedback system employed by the user during the surgery without the user performing the action of recording.

The data from the signal can be recorded in any medium such as memory readable by a computer, or human-decipherable output produced by the automated system, such as in real time.

The feedback system then generates audio, visual, or tactile indicators based on the received signal that is indicative of quantities measured by the sensors in the broach. The data can be recorded in the computer memory, and/or any observations by the user of the indicators perceived during the broaching step of the surgery can be recorded as well.

The user may adjust surgical techniques based on the indicators, and then continue impacting the rasp containing the sensor(s), perceiving indicators, optionally making record of any levels of indicators perceived, and optionally reacting to levels indicated. Following, the rasp is removed the rasp from the femur.

The broaching steps are repeated using a rasp containing the sensor(s) as described above, where the rasp is larger than the previously used rasps such that it increases the size of the cavity in the proximal femur. The cavity can then also be prepared using a powered rasp instrument, such as that described in U.S. Pat. No. 9,629,641 B2, the entire contents of which are herein incorporated by reference.

The hip replacement surgery or revision hip replacement surgery is then completed including implantation of the femoral component and preparation for and implantation of the acetabular component, and surgical wound closure and treatment. Optionally, the record(s) of at least one point of data derived from the signal of any sensor present within any of the rasp instruments during their use in the surgery can be accessed and reviewed to input further notes and data.

Figure 33:
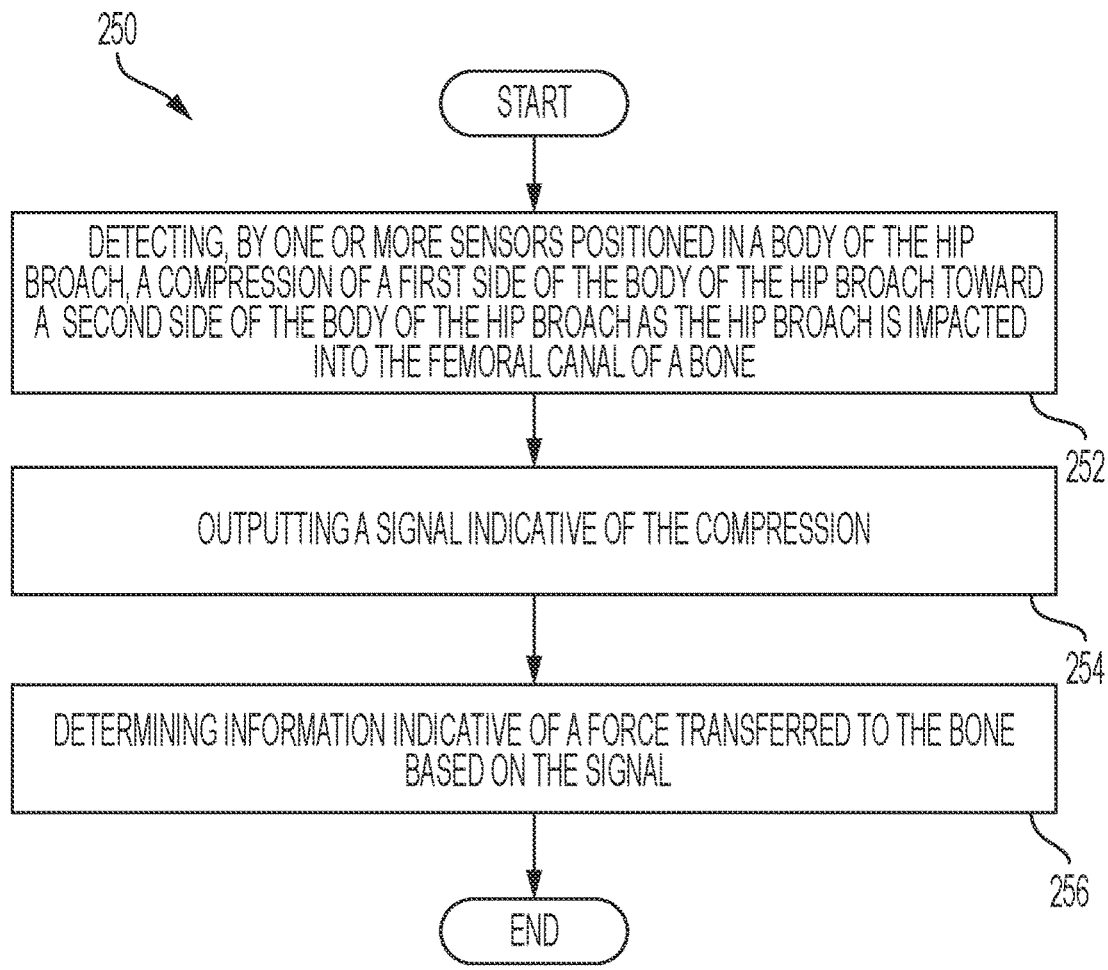
FIG. 33 illustrates a flowchart of an example method for impacting the hip broach into a femoral canal, according to an example implementation.

FIG. 33 illustrates a flowchart of an example method 250 for impacting the hip broach 100 into a femoral canal, according to an example implementation. The method 250 includes detecting, by the one or more sensors 112 positioned in the body 102 of the hip broach 100, a compression of the first side 104 of the body 102 of the hip broach 100 toward the second side 106 of the body 102 of the hip broach 100 as the hip broach 100 is impacted into the femoral canal of a bone, as shown at block 252. The method 250 also includes outputting a signal indicative of the compressive, as shown at block 254, and determining information indicative of a force transferred to the bone based on the signal, as shown at block 256.

Figure 34:
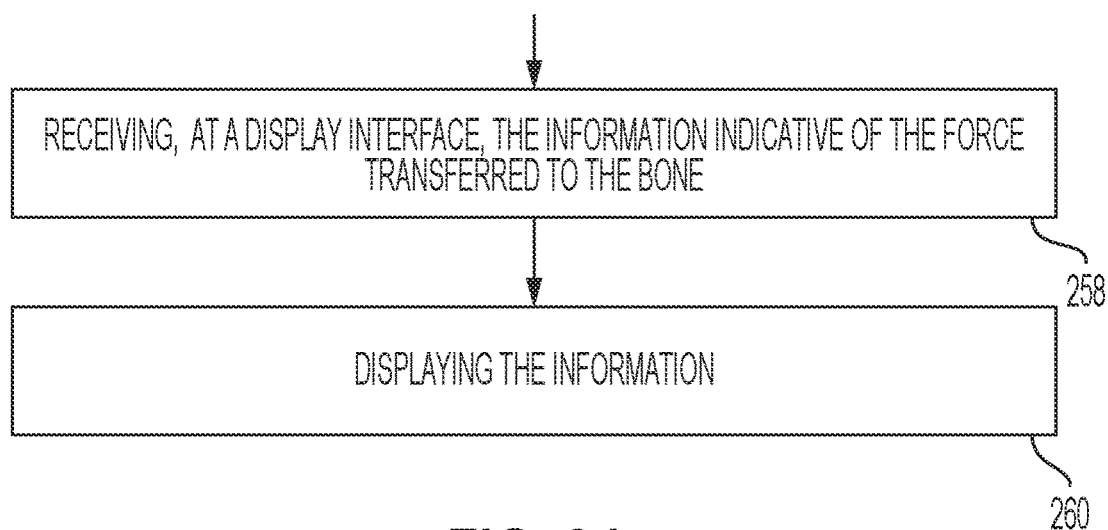
FIG. 34 illustrates a flowchart of an example method for use with the method shown in FIG. 33, according to an example implementation.

FIG. 34 illustrates a flowchart of an example method for use with the method 250 shown in FIG. 33, according to an example implementation. At block 258, additional functions include receiving, at the display interface, the information indicative of the force transferred to the bone. At block 260 additional functions include displaying the information.

By the term "substantially" used herein, it is meant that the recited characteristic, parameter, or value need not be achieved exactly, but that deviations or variations, including for example, tolerances, measurement error, measurement accuracy limitations and other factors known to skill in the art, may occur in amounts that do not preclude the effect the characteristic was intended to provide.

Different examples of the system(s), device(s), and method(s) disclosed herein include a variety of components, features, and functionalities. It should be understood that the various examples of the system(s), device(s), and method(s) disclosed herein may include any of the components, features, and functionalities of any of the other examples of the system(s), device(s), and method(s) disclosed herein in any combination, and all of such possibilities are intended to be within the scope of the disclosure.

The description of the different advantageous arrangements has been presented for purposes of illustration and description, and is not intended to be exhaustive or limited to the examples in the form disclosed. Many modifications and variations will be apparent to those of ordinary skill in the art. Further, different advantageous examples may describe different advantages as compared to other advantageous examples. The example or examples selected are chosen and described in order to best explain the principles of the examples, the practical application, and to enable others of ordinary skill in the art to understand the disclosure for various examples with various modifications as are suited to the particular use contemplated.

What is claimed is:

1. A method comprising:
    detecting, by one or more sensors positioned in a body of a component secured to a driving device at a proximal end of the component, a compression of the component as the component is impacted into a bone, wherein the compression is detected via a displacement of one or more of a first side of the body of the component toward a second side of the body of the component;
    determining information indicative of a force transferred to the bone based on a signal output from the one or more sensors indicating the compression of the body of the component as the component is impacted into the bone due to being impressed upon by the bone; and
    displaying, using a light indicator, a visual indication of the force transferred to the bone.

2. The method of claim 1, further comprising:
    causing the component to be detached from the driving device.

3. The method of claim 1, wherein detecting the compression includes using a piezo-electric sensor within the component to determine the impact force.

4. The method of claim 1, wherein the driving device is an impactor instrument.

5. The method of claim 1, further comprising:
    outputting an audible signal based on the determined force transferred to the bone.

6. The method of claim 5, wherein outputting the audible signal comprises:
    outputting the audible signal in real time during initial impaction.

7. The method of claim 1, further comprising:
    wirelessly transmitting the signal to a display interface.

8. The method of claim 1, further comprising:
    providing a tactile indicator based on the signal that is indicative of a quantity measured by the one or more sensors.

9. The method of claim 1, further comprising:
    outputting an audible or visual signal to a display interface based on the determined force transferred to the bone being above a threshold amount.

10. The method of claim 1, further comprising:
    providing alerts about whether the determined force transferred to the bone is above or below a threshold value.

11. The method of claim 1, further comprising:
    receiving, at a display interface, the information indicative of the force transferred to the bone; and
    displaying the information.

12. The method of claim 1, wherein the component further comprises one or more processors positioned in the component, wherein the one or more processors are coupled to the one or more sensors, and the method further comprises:
    receiving, at the one or more processors, the signal and processing the signal into the information indicative of the force transferred to the bone.

13. The method of claim 12, wherein the driving device is an impactor to apply the force for impacting the component into the bone, and wherein the method further comprises:
    controlling, by the one or more processors, the impactor based on the determined force transferred to the bone.

14. The method of claim 13, wherein the method further comprises:
    applying, by the one or more processors, a feedback loop to the impactor to prevent further broaching based on the determined force transferred to the bone being above a threshold amount.

15. The method of claim 13, wherein applying, by the one or more processors, the feedback loop to the impactor comprises:
    causing additional or less power to be applied by the impactor based on the determined force transferred to the bone.

16. The method of claim 1, wherein the component includes multiple sensors, and wherein the method further comprises:
    mapping the force along a length of the component, based on outputs of the multiple sensors, to identify an area along which the force is being experienced.

17. The method of claim 16, wherein mapping the force along the length of the component comprises:
  receiving outputs from the multiple sensors; and
  displaying the outputs of the multiple sensors to illustrate specific regions where stress is being experiencing on the component.

18. A method comprising:
  detecting, by multiple sensors positioned in a body of a component secured to a driving device, a compression of the component as the component is impacted into a bone;
  determining information indicative of a force transferred to the bone based on a signal output from the one or more sensors indicating the compression of the body of the component as the component is impacted into the bone due to being impressed upon by the bone;
  mapping the force along a length of the component, based on outputs of the multiple sensors, to identify an area along which the force is being experienced; and
  displaying, using a light indicator, a visual indication of the force transferred to the bone.

19. The method of claim 18, wherein mapping the force along the length of the component comprises:
  receiving outputs from the multiple sensors; and
  displaying the outputs of the multiple sensors to illustrate specific regions where stress is being experiencing on the component.

* * * * *